US007541032B2

(12) United States Patent
Figdor et al.

(10) Patent No.: US 7,541,032 B2
(45) Date of Patent: Jun. 2, 2009

(54) **ANTIGEN UPTAKE RECEPTOR FOR *CANDIDA ALBICANS* ON DENDRITIC CELLS**

(75) Inventors: Carl Gustav Figdor, Den Bosch (NL); Ruurd Torensma, Nijmegen (NL)

(73) Assignee: Stichting Katholieke Universiteit, Nijmegen (NL)

( * ) Notice: Subject to any disclaimer, the term of this patent is extended or adjusted under 35 U.S.C. 154(b) by 301 days.

(21) Appl. No.: 10/524,395

(22) PCT Filed: Sep. 19, 2003

(86) PCT No.: PCT/IB03/04661

§ 371 (c)(1),
(2), (4) Date: Dec. 27, 2005

(87) PCT Pub. No.: WO2004/026326

PCT Pub. Date: Apr. 1, 2004

(65) Prior Publication Data

US 2006/0233805 A1      Oct. 19, 2006

Related U.S. Application Data

(60) Provisional application No. 60/412,599, filed on Sep. 20, 2002.

(51) Int. Cl.
*A61K 39/395* (2006.01)
(52) U.S. Cl. ............... 424/143.1; 424/152.1; 424/172.1
(58) Field of Classification Search ........................ None
See application file for complete search history.

(56) References Cited

U.S. PATENT DOCUMENTS

| 6,548,275 B2 | 4/2003 | Goldenberg |
| 6,605,279 B2 | 8/2003 | Freeman et al. |
| 7,285,642 B2 * | 10/2007 | Figdor et al. ............. 530/387.1 |
| 2003/0134297 A1 * | 7/2003 | Olson et al. .................... 435/6 |
| 2003/0232745 A1 | 12/2003 | Olson et al. |

FOREIGN PATENT DOCUMENTS

| WO | WO 93/01820 | 2/1993 |
| WO | WO 95/32734 | 12/1995 |
| WO | WO 96/23882 | 8/1996 |
| WO | WO 98/02456 | 1/1998 |
| WO | WO-9828332 | 7/1998 |
| WO | WO 98/41633 | 9/1998 |
| WO | WO 98/49306 | 11/1998 |
| WO | WO-9855508 | 12/1998 |
| WO | WO 00/63251 | 10/2000 |
| WO | WO 02/50119 | 6/2002 |

OTHER PUBLICATIONS

Rosati et al. (Cell. Immunol., 162:256-264, 1995).*

Fè d'Ostiani, C., et al., "Dendritic Cells Discriminate between Yeasts and Hyphae of the Fungus *Candida albicans*: Implications for Initiation of T Helper Cell Immunity In Vitro and In Vivo," J. Exp. Med., 191(10):1661-1673 (2000).

Forsyth, C. B., et al., "Interaction of the Fungal Pathogen *Candida albicans* with Integrin CD11b/CD18: Recognition by the I Domain Is Modulated by the Lectin-Like Domain and the CD18 Subunit," The Journal of Immunology, 161:6198-6205 (1998).

Marth, T., et al., "Regulation of Interleukin-12 by Complement Receptor 3 Signaling," The Journal of Experimental Medicine, 185(11):1987-1995 (1997).

Netea, M. G., et al., "Immune sensing of *Candida albicans* requires cooperative recognition of mannans and glucans by lectin and Toll-like receptors," The Journal of Clinical Investigation, 116(6):1642-1650 (2006).

Szabo, I., et al., "Modulation of Macrophage Phagocytic Activity by Cell Wall Components of *Candida albicans*," Cellular Immunology, 164:182-188 (1995).

Amersdorfer et al., *Infection and Immunity*, 65, pp. 3743-3752 (1997).

Andre et al., *Journal of Virology*, 72(2), pp. 1497-1503 (1998).

Baribaud, Frederic, et al., "Functional and Antigenic Characterization of Human, Rhesus Macaque, Pigtailed Macaque, and Murine DC-SIGN," *Journal of Virology*, 75(21), pp. 10281-10289 (2001).

Berkower, I., et al., "Chimeric HIV-1 Envelope GP120-Hepatitis B Core Antigen (HbcAg) Fusion Proteins for HIV-1 Vaccines," FASEB Journal, 10(6):A1082 (1996).

Biosis Database, Prev 197866028654 & Kataoka et al., *Cancer Research*, 38(5), pp. 1202-1207 (1987).

Cohen, *Science*, 287, p. 1567 (2000).

Curtis, BM, et al., "Sequence and Expression of a Membrane-Associated C-type Lectin that Exhibits CD4-Independent Binding of Human Immunodeficiency Virus Envelope Glycoprotein GP 120," Proc. Natl. Acad. Sci. USA 89:8356-8360 (1992).

Eck J., et al., "Cloning of the Mistletoe Lectin Gene and Characterization of the Recombinant A-Chain," European Journal of Biochemistry, 264:775-784 (1999).

(Continued)

*Primary Examiner*—Mark Navarro
*Assistant Examiner*—Brian J Gangle
(74) *Attorney, Agent, or Firm*—Ropes & Gray LLP

(57) ABSTRACT

Dendritic cells (DC) that express the type II C-type lectin DC-SIGN (CD209) are located in the submucosa of tissues, where they mediate HIV-1 entry. Interestingly, the pathogen *Candidaalbicans*, the major cause of hospital-acquired fungal infections, is found at similar sites. Here it is demonstrated that DC-SIGN is able to bind *Candida albicans* both in DC-SIGN transfected cell lines and in human monocyte derived DC. Moreover, in immature DC, DC-SIGN is able to internalize *Candida* in specific DC-SIGN enriched vesicles, distinct from those containing the mannose receptor (MR; CD206), which is another *Candida* receptor on DC. Together, these results demonstrate that *C. albicans* has two major receptors on human monocyte derived DC, these receptors being DC-SIGN and MR. Targeting of DC-SIGN offers novel opportunities to combat chronic forms of candidiasis.

16 Claims, 19 Drawing Sheets

OTHER PUBLICATIONS

Engering, Anneke, et al., "The Dendritic Cell-Specific Adhesion Receptor DC-SIGN Internalizes Antigen for Presentation to T Cells," *J. of Immun.*, 168, pp. 2118-2126 (2000).

FDA Approves Second Indication for Monolclonal Antibody, Jun. 28, 1993, printed on Nov. 12, 2004 from http://www.fda.gov/bbs/topics/ANSWERS/ANS00506.html, Jun. 28, 1993.

Feinberg, Hadar, et al., "Structural Basis for Selective Recognition of Oligosaccharides by DC-SIGN and SC-SIGNR," *Science*, 294, pp. 2163-2166 (2001) (with Supplementary Material published electronically on the *Science* website, 6 pgs.).

Geijtenbeek, et al., "Identification of Different Binding Sites in the Dendritic Cell-Specific Receptor DC-SIGN for Intercellular Adhesion Molecule 3 and HIV-1," *J. Biol. Chem.*, 227(13), pp. 11314-11320 (2002).

Geijtenbeek, Teunis, B.H., et al., "Identification of DC-SIGN, a Novel Dendritic Cell-Specific ICAM-3 Receptor that Supports Primary Immune Responses," *Cell*, 100, pp. 575-585 (2000).

Geijtenbeek, Teunis, B.H., et al., *Cell*, 100, pp. 587-597 (2000).

Gruber, Andreas, et al., "Functional Aspects of Binding of Monoclonal Antibody DCN46 to DC-SIGN on Dendritic Cells," *Immunology Letters*, 84, pp. 103-108 (2002).

Harlow and Lane, Antibodies, A Laboratory Manual.

Janeway, Charles, A., Jr., et al., *Immunobiology*, (5th ed.), Garland Publishing, New York, p. 691 (2001).

Knight SC., et al., "Bone Marrow-Derived Dendritic Cells, Infection with Human Immunodeficiency Virus, and Immunopathology," Annual Review Immunology 15:593-615 (1997).

Manca F. et al., "Dendritic Cells Are Potent Antigen-Presenting Cells for In Vitro Induction of Primary Human CD4+ T-Cell Lines Specific for HIV GP 120," Journal of Acquired Immune Deficiency Syndromes 7:15-23 (1994).

Package insert for Orthoclone OKT3 Sterile Solution (murumonab-CD3) from Ortho Biotech Products LP, Raritan, NJ, Revised Mar. 2001.

Pohlmann, Stefan, et al., "DC-SIGN Interactions with Human Immunodeficiency Virus Type 1 and 2 and Simian Immunodeficiency Virus," *J. of Virology*, 75(10), pp. 4664-4672 (2001).

Product Information for Affinity Purified anti-human CD209 (DC-SIGN) antibody, from eBioscience, printed on Jan. 5, 2004 from http://www.ebioscience.com/ebioscience/specs/antibody_14/14-2099.htm.

Purified Mouse Anti-Human Monoclonal Antibody, BD PharMingen Technical Data Sheet, BD Biosciences Product Information sheet, Catalog No. 551186, May 1, 2001.

Sequence Alignment of Curtis et al., PNAS 89: 8356-8360 (1992) with SEQ ID No. 2 from U.S. Appl. No. 09/719,961.

Soilleux, E.J., et al., "Cutting Edge: DC-SIGN; a Related Gene, DC-SIGNR; and CD23 Form a Cluster on 19p. 13,[1,2]" The Journal of Immunology, 165:2937-2942 (2000).

Steinbrook, R., "One Step Forward, Two Steps Back—Will There Ever Be an AIDS Vaccine?," N. Engl. J. Med., 357:2653-2655 (2007).

Steinman, *Cell*, 287, pp. 491-494 (2000).

Taken, P.J., et al., "Effective induction of naive and recall T-cell responses by targeting antigen to human dendritic cells via a humanized anti-DC-SIGN antibody," Blood, 106(4):1278-1285 (2005).

Toda, et al., *Immunology*, 92, pp. 111-117 (1997).

Tsunetsugu-Yokota, Y. et al., "Efficient Virus Transmission from Dendritic Cells to CD4+ T Cells in Response to Antigen Depends on Close Contact through Adhesion Molecules," Virology 239:259-268 (1997).

Vakeva, Antti, P., et al., "Myocardial Infarction and Apoptosis After Myocardial Ischemia and Reperfusion," *Circulation*, 97, pp. 2259-2267 (1998).

Woodle, E.S., et al., Translplantation, 68, pp. 608-616 (1999).

Yan et al., "β-Glucan, a "Specific" Biologic Response Modifier That Uses Antibodies to Target Tumors for Cytotoxic Recognition by Leukocyte Complement Receptor Type 3 (CD11b/CD18)," The Journal of Immunology, 163(6):3045-3052 (1999).

Zoeteweij, JP. et al., "HIV-Dendritic Cell Interatcions Promote Efficient Viral Infection of T Cells," Journal of Biomedical Science 5:253-259 (1998).

* cited by examiner

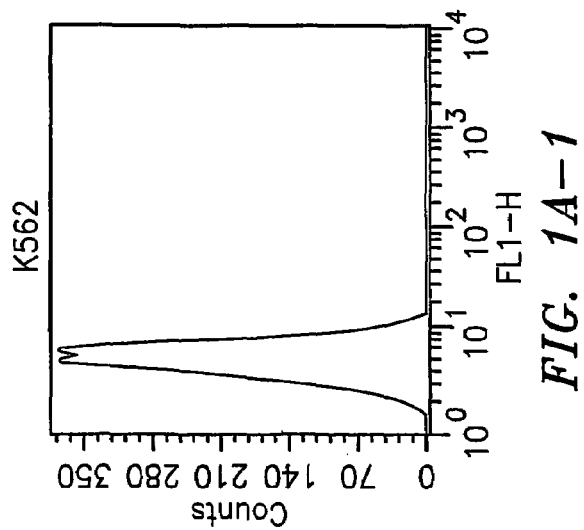
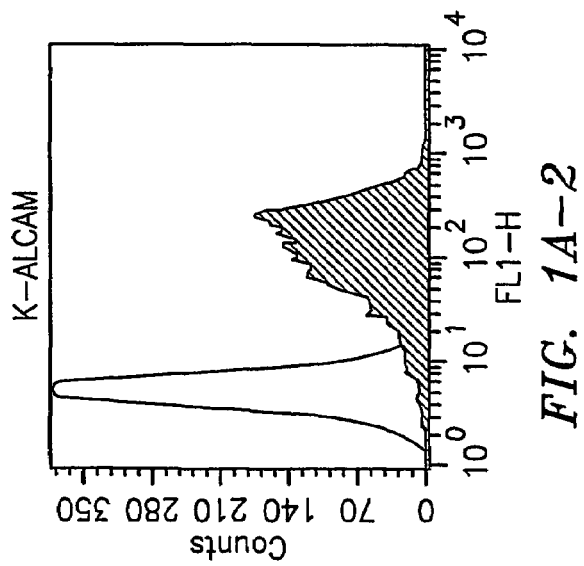
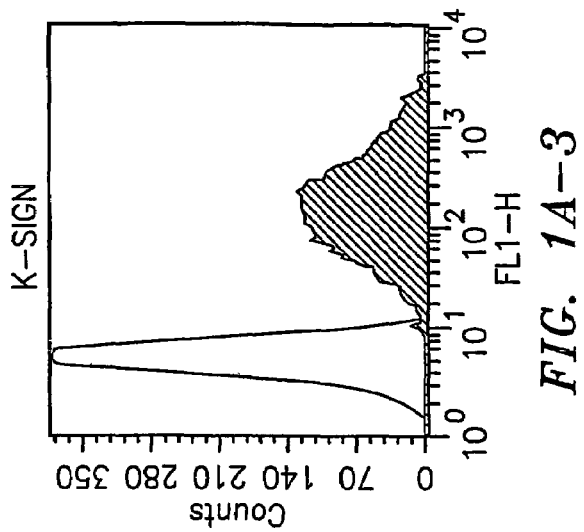
FIG. 1A-1  FIG. 1A-2  FIG. 1A-3

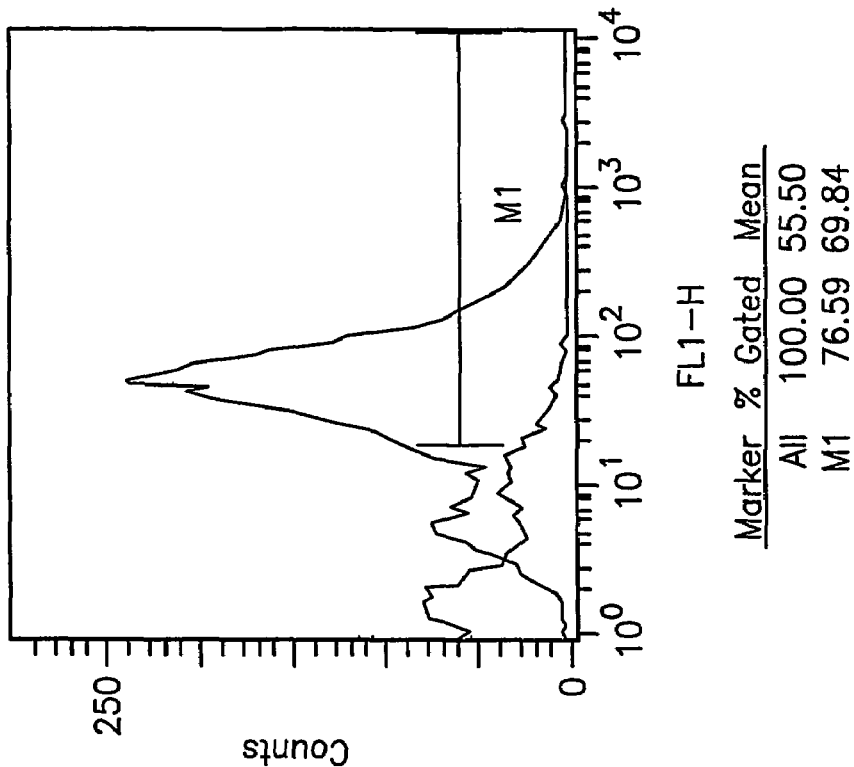
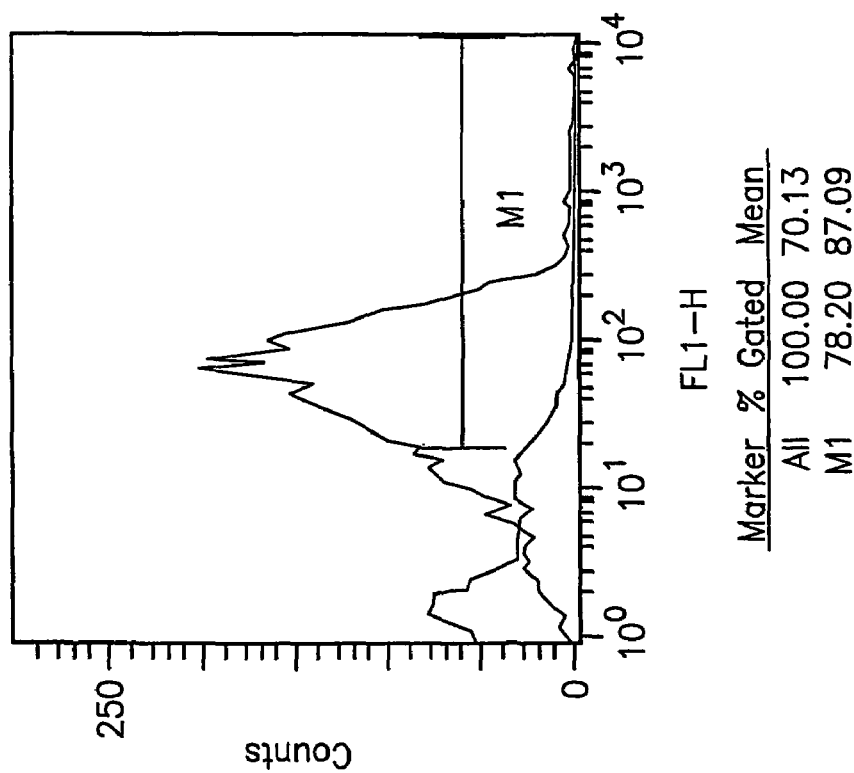
FIG. 3C-2
FIG. 3C-1

Candida-FITC

β2-integrins

Merged

Candida-FITC

ALCAM

Merged

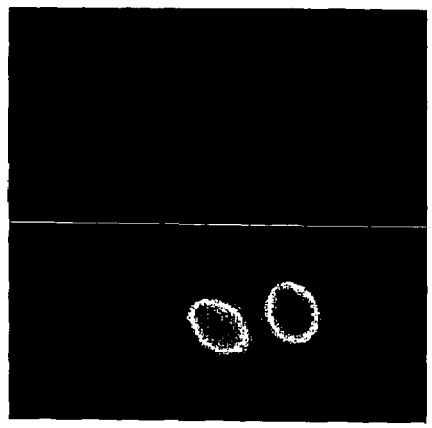
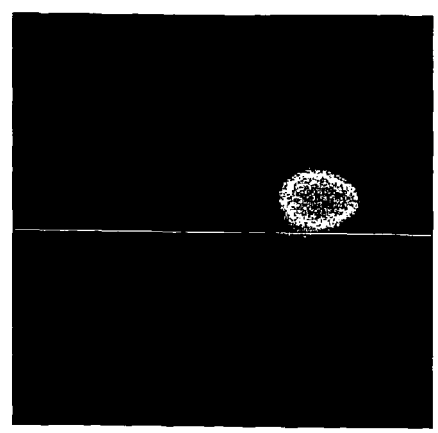
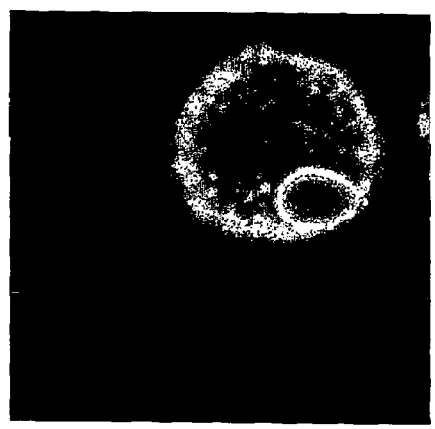
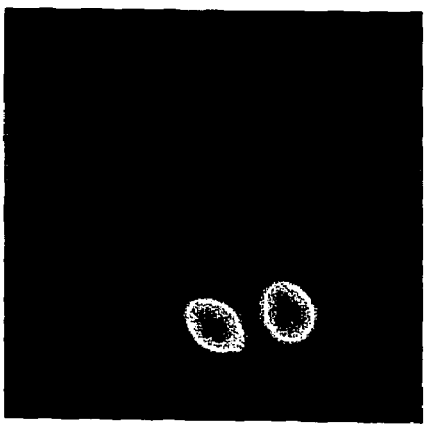
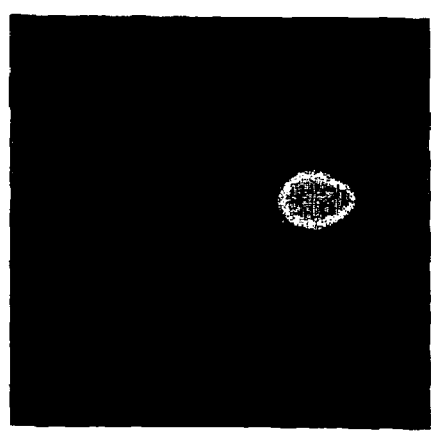
Candida-FITC / DC-SIGN / Merged
FIG. 4C-1, FIG. 4C-2, FIG. 4C-3, FIG. 4C-4, FIG. 4C-5, FIG. 4C-6

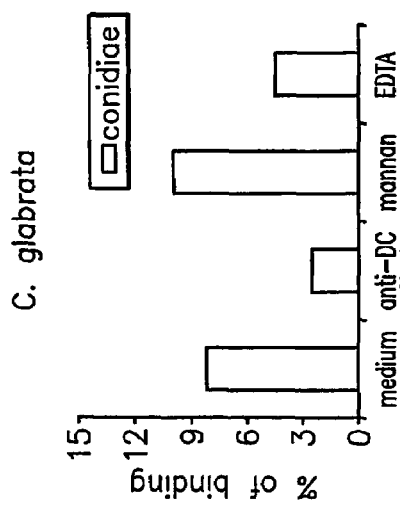
FIG. 8A
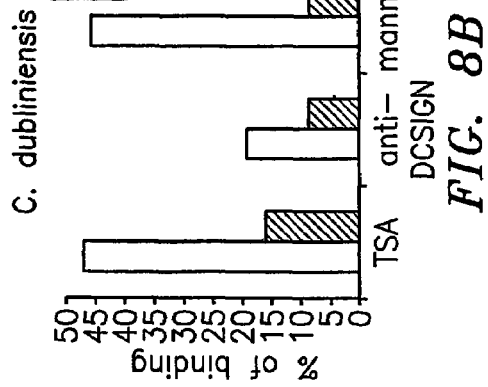
FIG. 8B
FIG. 8C
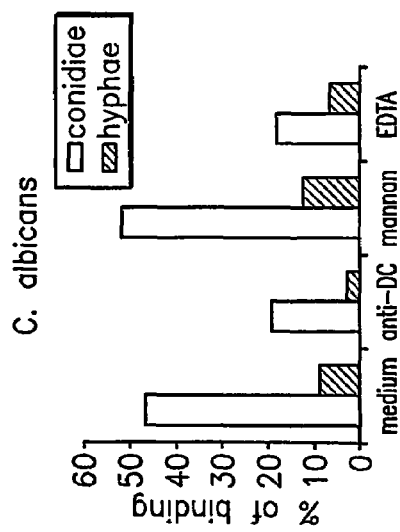
FIG. 8D
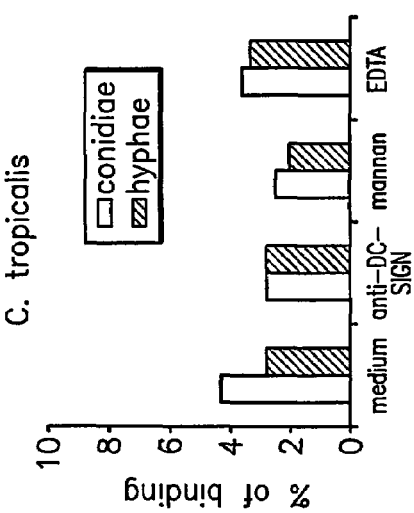
FIG. 8E
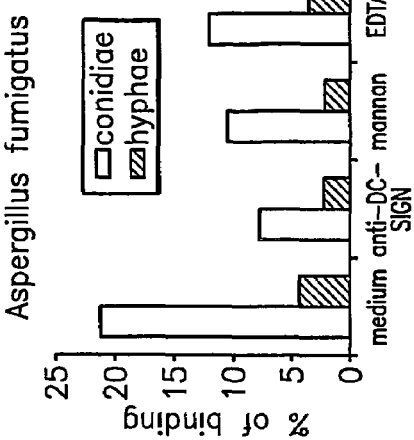
FIG. 8F
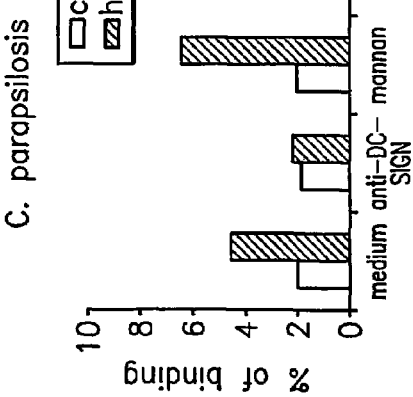

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Artificial peptidomimetic for beta-1,
      2-oligomannoside

<400> SEQUENCE: 1

Phe His Glu Asn Trp Pro Ser
 1               5
```

ANTIGEN UPTAKE RECEPTOR FOR *CANDIDA ALBICANS* ON DENDRITIC CELLS

This application is the U.S. National Phase Application under 35 USC 371 of International Application Number PCT/IB/03/04661, filed on 9/19/2003, which claims benefit of U.S. Provisional Application No. 60/412,599, filed on Sep./20/2002.

TECHNICAL FIELD

This disclosure relates to compounds, compositions and methods for preventing pathogen uptake on dendritic cells via DC-SIGN. More particularly, this disclosure relates to the use of antibodies against DC-SIGN and their use in preventing infection by pathogens. The disclosure further relates to the use of antigenic portions of pathogens which bind to DC-SIGN to mount an immune response to the pathogen.

BACKGROUND

Epithelial surfaces form the first line of defense against microbes. A small proportion of incoming microbes that enter at sites of microlesions is handled by antigen-presenting cells (APCs), which are mostly dendritic cells (DC) (Steinman, 1991).

*Candida albicans* is among the most frequently isolated fungal pathogen in humans that invade the mucosal surface (Edwards, 1991). As the major cause of hospital-acquired fungal infections (Sternberg, 1994), the recognition of *C. albicans* by cell surface receptors has major pathogenetic consequences. Nevertheless, only limited information is available on the molecular mechanisms involved in recognition of this fungus. *C. albicans* can switch from a unicellular yeast form into various filamentous forms, all of which can be found in infected tissues (Odds, 1987). The ability to reversibly switch between these forms is thought to be important for *Candida's* virulence. Several studies now demonstrate that dendritic cells can bind and phagocytose fungi like *Candida albicans* (d'Ostiani et al., 2000; Forsyth et al., 1998; Huang et al., 2001). Reports have indicated that protection from mucocutaneous candidiasis relies on cell-mediated immunity induced after processing of *Candida* and presentation by DC to prime T cells (Newman and Holly, 2001).

Recent studies in mice demonstrate that while the yeast form activates dendritic cells for IL-12 production and priming of T helper type 1 (Th1) cells, the hyphal form inhibits IL-12 and Th1 priming and induces IL-4 production (d'Ostiani et al., 2000). These results indicate that dendritic cells fulfill the requirement of a cell uniquely capable of sensing the two forms of *C. albicans* (d'Ostiani et al., 2000). In addition, it was recently reported that human dendritic cells are also able to bind *C. albicans*, and that this interaction is mediated by the mannose -fucose receptor (FR, CD206), as observed also on macrophages (Newman and Holly, 2001).

Both the yeast form and the hyphae form of yeast are phagocytosed by dendritic cells (d'Ostiani et al, 2000). But each form is treated differently by the cells and results in a different response. Phagocytosis of the yeast form activates dendritic cells for interleukin-12 production and priming of T helper type 1 (Th1) cells thereby aiding in mounting an immune response. In contrast, phagocytosis of the hyphal form inhibited IL-12 production and Th1 priming and induced IL-4 production which suppresses the immune response and favors Th2 cells. Whereas Th1 cells mediate phagocyte-dependent protection and are the principal mediators of acquired protective immunity, Th2-like reactivity is frequently observed in patients with *Candida*-related pathology (d'Ostiani et al., 2000).

There is also evidence that the type of response depends upon the receptor used to take up the pathogenic organism. *Candida* yeast uptake is more sensitive to mannan inhibition than is uptake of the *Candida* hyphae. This suggested that receptors in addition to the mannose receptor are involved in uptake of *Candida* (d'Ostiani et al., 2000). Receptors for antigen capture on dendritic and phagocytic cells vary in their ligand and specificity and mode of delivery to antigen-processing compartments (d'Ostiani et al., 2000; Aderem and Underhill, 1999; Vidarsson and van de Winkel, 1998; Mosser and Karp, 1999). The mannose receptor-mediated phagocytosis of nonopsonized *C. albicans* resulted in the generation of proinflammatory cytokines (Yamamoto et al, 1997), and the mannose receptor-mediated phagocytosis of zymosan initiated IL-12 production in phagocytes (Shibata et al, 1997). In contrast, interaction with receptors other than the mannose receptors, including CR3 (Forsyth et al, 1998), led to suppression of the immune response to *C. albicans* (Szabo et al., 1995) and other fungi (Marth and Kelsall, 1997).

Recently, a novel C-type lectin, designated DC-specific ICAM-grabbing non-integrin (DC-SIGN; CD209) was isolated from monocyte-derived dendritic cells (Geijtenbeek et al., 2000a). It was discovered that besides the capacity of DC-SIGN to bind and capture HIV-1 at mucosal sites of initial infection and protecting the virus from degradation for subsequent transport by DC to lymphoid organs (Geijtenbeek et al., 2000b), DC-SIGN acts as a binding partner for ICAM-3 (Geijtenbeek et al., 2000a). This early contact may enable the T cell receptor (TCR) to scan for processed antigens, allowing the initiation of primary immune responses. DC-SIGN also displays a high affinity for ICAM-2, supporting transendothelial migration of DC and DC trafficking (Geijtenbeek et al., 2000c).

Naive T cells are characterized by a high expression of ICAM-3 which is a member of the IgG supergene family and is rapidly downregulated after activation (Vazeux et al., 1992). It was observed that DC-SIGN mediates adhesion between dendritic cells and ICAM-3 on naive T cells and appears to be essential for DC-induced T cell proliferation (Geijtenbeek et al., 2000a; Steinman, 2000).

Modulation of immune responses can be achieved by affecting the interaction between dendritic cells and T cells (see WO 00/63251, the contents of which are specifically incorporated herein by reference in their entirety, which describes the finding of DC-SIGN on dendritic cells in healthy persons). Immune responses can be inhibited or prevented by preventing the interaction of DC-SIGN on dendritic cells with receptors on T cells, e.g., by using antibodies specific for DC-SIGN. Alternatively, an immune response to an antigen can be potentiated by binding the antigen to DC-SIGN on dendritic cells such that the antigen plus DC-SIGN is taken up by dendritic cells and processed and presented to T cells.

WO 96/23882 describes a murine and human receptor with C-type lectin domains that is abundantly expressed on the surface of dendritic cells and thymic epithelial cells. The murine receptor—named "DEC-205"—is described as a 205 kDa protein with an isoelectric point of about 7.5 that contains 10 C-type lectin domains and that is homologous to the macrophage mannose receptor (MMR).

WO 96/23882 further describes monoclonal and polyclonal antibodies against DEC-205. However, these antibodies were not able to block dendritic cell function. In particular, monoclonal and polyclonal anti-DEC-205 antibodies were unable to inhibit the interaction between dendritic cells and helper T cells, both in vitro (as determined by the inability of anti-DEC-205 to inhibit allogenic T cell proliferation in a one way mixed leukocyte reaction) and in vivo (as determined by the inability of anti-DEC-205 to inhibit an in vivo response, i.e. in a local graft-versus-host (GVH) reaction). These results suggest that the DEC-205 receptor is not involved in dendritic cell-T-cell interaction (i.e. adhesion) and that the anti-DEC-205 antibodies cannot be used to modulate the immune response.

Curtis et al. (1992), as well as in WO 93/01820, describe a non-CD4 gp120 receptor isolated and cloned from human placenta tissue. This gp120 receptor is expressed on mammalian cells which do not exhibit high levels of CD4, such as placenta, skeleton muscle, brain, neural and mucosal cells, as well as other tissues and cells including colon, thymus, heart, T cells, B cells and macrophages (but not in the liver or the kidney). The amino acid sequence of the C-type lectin gp120 receptor disclosed in SEQ ID NOs:1 and 2 of WO 93/01820 has a high degree of sequence homology (>98%) with the C-type lectins that were found to be present on dendritic cells (WO 00/63251; Geijtenbeek et al., 2000a).

Curtis et al. (1992) and WO 93/01820 further discuss the role this C-type lectin receptor plays in the infection of the aforementioned cells/tissues with HIV, i.e. by binding the major HIV envelope glycoprotein gp120 prior to internalization of the virion into the cell. It was found that inhibition of the C-type lectin gp120 receptor could reduce or inhibit HIV infection of these cells/tissues. As suitable inhibitors, WO 93/01820 discloses mannose carbohydrates, fucose carbohydrates, plant lectins such as concanavalin A, specific antibiotics such as pradimicin A, and sugars such as N-acetyl-D-glucosamine and galactose (which however are described as less potent). These compounds and compositions containing them are used either in vitro or in vivo to inhibit the binding of HIV to the cell surface.

Neither Curtis et al. (1992) nor WO 93/01820 mentions or suggests the presence of a C-type lectin on dendritic cells, nor do these references mention or suggest their role in dendritic cell—T cell interaction during the initial stages of an immune response nor do they mention or suggest that the C-type lectin binds to any yeast or fungi or specifically to *C. albicans*.

WO 95/32734 describes FcγRII (CD32) bridging (or crosslinking) compositions and their use in modulating the immune response to specific antigens. This reference is based upon the finding that the bridging of FcγRII (CD32) molecules on antigen presenting cells (APCs) impairs the expression of the essential co-stimulatory molecules B7½ (i.e. prevents their up-regulation) and thereby impairs the expression of (i.e. causes the down-modulation of) the adhesion molecule ICAM-3, with the functional consequence of an impaired capacity of the monocytes to co-stimulate the activation of antigen-specific T cells (i.e. resulting in the modulation of antigen-specific T cell unresponsiveness). The bridging agent is chosen from aggregated human IgG molecules or Fc-fragments thereof; bi- or multivalent monoclonal antibodies to FcγRII or fragments thereof, or a fusion of two or more human IgG Fc parts.

WO 95/32734 is therefore directed towards modulating (i.e. inhibiting) the co-stimulation signal required for T cell activation (i.e. besides the primary signal of TCR/CD3 interaction), in particular to induce proliferation and maturation into effector cells. WO 95/32734 is not directed towards modulating dendritic cell—yeast cell interaction.

WO 98/02456 discloses a group II human C-type lectin isolated from a stimulated human macrophage library. WO 98/49306 discloses a group IV C-type lectin present in human pancreatitis-associated protein ("PAP"). WO 98/41633 discloses a group V human C-type lectin isolated from a human tumor clone.

WO 98/02456, WO 98/49306 and WO 98/41633 further disclose methods for producing antibodies against these C-type lectins. However, none of these references relates to interaction between C-type lectins and yeast.

Dendritic cells (DC) are antigen-presenting cells that capture antigens in the peripheral tissues and migrate via lymph or blood to the T cell area of draining lymph nodes and spleen. Here they present processed antigens to naive T cells, initiating antigen-specific primary T cell responses.

DC are unique in their ability to interact with and activate resting T cells. However, prior to publication of WO 00/63251 and Geijtenbeek et al. (2000a), it was largely unknown how DC-T cell contact is initiated and regulated. Therein, the role of ICAM-3 in DC-T cell interactions was investigated. It was demonstrated that although DC strongly adhere to ICAM-3, this adhesion is not mediated by LFA-1, αD or any other integrin. In the search for this novel ICAM-3 receptor on DC, a C-type lectin receptor, designated DC-SIGN, which is preferentially expressed by DC was cloned. Besides its prominent role in DC-T cell clustering and initiation of T cell responses, it was discovered that DC-SIGN is a major HIV-1 receptor involved in infection of DC and subsequent HIV-1 transmission to T cells. Thus HIV-1 and resting T cells exploit a similar highly expressed receptor to interact with DC.

The publications and other materials used herein to illuminate the background of the invention, and in particular, cases to provide additional details respecting the practice, are incorporated herein by reference, and for convenience, are referenced by author and date in the text and respectively grouped in the appended List of References.

SUMMARY

In one aspect, the present disclosure relates to binding microorganisms, such as, for example, *C. albicans*, to the C-type lectin DC-SIGN on dendritic cells.

In a second aspect, this disclosure relates to inhibiting binding of microorganisms to DC-SIGN by using one or more compounds including, for example, β-1,2-oligomannoside and antibodies to DC-SIGN.

Treatment of animals, including humans, infected by microorganisms that bind to DC-SIGN, can be effected by treating said animals with agents that effectively inhibit the binding between said microorganisms and DC-SIGN. In particular, this covers treatment of animals with candidiasis.

A further aspect of the disclosure concerns the method of targeting an antigen of a pathogen to a dendritic cell to increase an immune response to the pathogen without causing a suppression of the immune response.

BRIEF DESCRIPTION OF THE DRAWINGS

FIGS. 1A-F illustrate that DC-SIGN specifically binds the yeast form of *Candida albicans*. FIGS. 1A-1, 1A-2 and 1A-3 show that K562 transfectants stably express DC-SIGN and ALCAM. FIG. 1B shows the binding of K-ALCAM cells and of K-SIGN cells to *C. albicans* coated beads, ICAM-3-Fc coated beads, and to ALCAM-Fc coated beads. FIG. 1C shows the binding of both K-ALCAM cells and K-SIGN cells to *C. albicans* and to ICAM-3 in the presence of no inhibitor, anti-DC-SIGN antibody AZN-D1, or EGTA. FIG. 1D illustrates that the *C. albicans* binding to DC-SIGN increases with an increase of the yeast:cell ratio. FIG. 1E illustrates that the binding of *C. albicans* to DC-SIGN increases with time. FIG. 1F shows that *C. albicans* binds to K562 transfected with DC-SIGN but not to K562 transfected with mutated DC-SIGN, L-SIGN or ALCAM and that the specific binding to DC-SIGN is inhibited by antibodies to DC-SIGN and by EGTA.

FIG. 2 shows that both live and heat-killed (at 56° C. or 100° C.) yeast forms of *C. albicans* are bound by DC-SIGN and that this binding is inhibited by anti-DC-SIGN antibodies and by EGTA.

FIG. 3C-1 shows a FACS analysis of staining immature DC with an antibody to DC-SIGN (AZN-D1) and FIG. 3C-2 shows a FACS analysis of staining immature DC with an antibody to the mannose receptor.

FIGS. 4A-E demonstrate that DC-SIGN mediates phagocytosis of *Candida albicans* in imDC. Confocal microscopy images of immature DC show that binding of FITC labeled *C. albicans* (green) co-localizes (Merge) with Cy5 labeled DC-SIGN (blue). Labeling of $\beta_2$-integrins (NKI-L19), ALCAM (NKI-L50), and mannose receptor are used as controls. FIGS. 4A1-6 show staining of $\beta_2$ integrin and *Candida*. FIGS. 4B1-6 show staining of ALCAM and *Candida*. FIGS. 4C1-6 show staining of DC-SIGN and *Candida*. FIG. 4D shows staining of mannose receptor and *Candida*. FIG. 4E shows staining of DC-SIGN and *Candida* in the presence of mannose (inhibiting MR).

FIG. 5 shows the effect of a variety of agents upon the binding of immature dendritic cells to *C. albicans*.

FIG. 6 shows the binding of conidiae and of hyphae to K-SIGN cells for different strains of live *C. albicans* and *C. dubliniensis*.

FIGS. 8A-F show binding of various species of *Candida* as well as *Aspergillus fumigates* to K-SIGN in the presence of medium, anti-DC-SIGN antibodies, mannan and EDTA. Results are shown for both conidiae and hyphae (except for *C. glabrata*).

DETAILED DESCRIPTION OF PREFERRED EMBODIMENTS

Figure 1B:
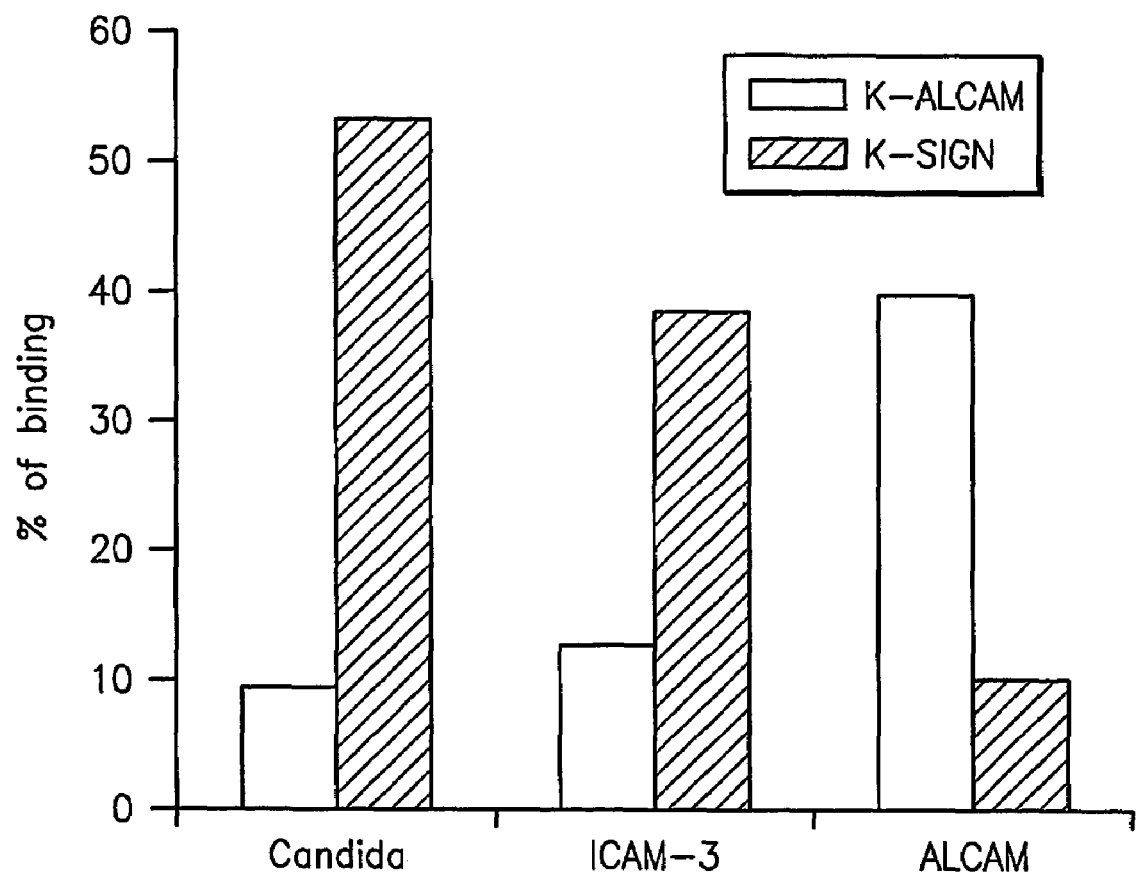

*C. albicans*, both as a commensal as well as a true pathogen, is found on areas (submucosa) highly enriched in DC-SIGN positive dendritic cells. In addition to viruses (HIV-1, SIV, Ebola) (Geijtenbeek et al., 2000b; Alvarez et al., 2002; Baribaud et al., 2001) and parasites (Leishmania) (Colmenares et al., 2002), the C-type lectin DC-SIGN has now been found to also bind yeast (*C. albicans*). Accordingly, C-type lectins on dendritic cells are major pathogen recognition receptors (Figdor et al., 2002). Distinct from the Toll like receptors (Medzhitov and Janeway, 2000), they mediate antigen uptake rather than activating dendritic cells. The binding is via a β-1,2-oligomannoside on *C. albicans* and other microorganisms. Thus other microorganisms comprising β-1,2-oligomannoside on their cell surface will bind to dendritic cells. The binding of these microorganisms to dendritic cells can be blocked by a variety of compounds as discussed below. Use of these compounds can prevent or alleviate infection by said microorganisms.

*C. albicans* has two major receptors on human monocyte derived DC, these being DC-SIGN and the mannose receptor (MR). DC-SIGN is expressed at sites in the skin (dermis) and the mucosa (Geijtenbeek et al., 2000b) where *C. albicans* is known to enter the host. DC-SIGN positive DC might therefore, through these C-type lectin receptors, form the first encounter with these pathogens and initiate an immune response (d'Ostiani et al., 2000; Newman and Holly, 2001).

Although not wishing to be bound by the proposed theory, it is believed, in accord with the publications by Yamamoto et al. (1997), Shibata et al. (1997), Forsyth et al. (1998), Marth and Kelsall (1997) and Szabo et al. (1995) as set forth by d'Ostiani et al. (2000), that the type of immune response to a pathogen, e.g. *Candida*, infection depends upon the receptor used to phagocytose the pathogen. It is believed that uptake via the mannose receptor generates a positive immune response (see, e.g., Yamamoto et al. (1997) and Shibata et al. (1997)) whereas uptake via certain other receptors leads to suppression of the immune response to *C. albicans* or other pathogen (see, e.g., Forsyth et al. (1998), Marth and Kelsall (1997) and Szabo et al. (1995)). It is here shown that pathogens such as *Candida* do bind to dendritic cells via DC-SIGN and it is theorized that uptake via DC-SIGN on dendritic cells results in a suppression of the immune response. Consequently it is proposed that uptake of *Candida* or other pathogens via the mannose receptor leads to a positive immune response whereas uptake of the pathogens via DC-SIGN leads to a suppression of the immune response. It is proposed that inhibiting the uptake of pathogens via DC-SIGN will help prevent a suppression of the immune response and *Candida*-related or other pathogen-related pathology. Preventing binding of the pathogen to DC-SIGN while allowing binding of the pathogen to mannose receptors is proposed to be a useful method to promote a proper response to promote an immune response against the pathogen. Some pathogens are destroyed through a Th1 response while others rely on a Th2 response to be effectively eliminated.

Again not wishing to be bound by the proposed theory, the finding reported herein that *Candida* and other pathogens are able to bind to dendritic cells via DC-SIGN leads to the proposal that a favorable immune response will be aided by administration of antigens of the infecting pathogen to a patient. In this method an antigen, e.g., a purified antigen such as one on the surface of a pathogen such as *C. albicans*, is administered to a person. The antigen can be taken up by dendritic cells via DC-SIGN, processed by the dendritic cells and presented to T cells thereby resulting in promotion of an immune response against the pathogen. If the antigen is one that does not naturally bind to DC-SIGN or even if it does, binding of the antigen to dendritic cells can be promoted by targeting the antigen to the dendritic cells, e.g., by binding the antigen to an antibody which binds to DC-SIGN. Methods of binding an antigen to an antibody are well known to those of skill in the art. See, e.g., U.S. Pat. No. 6,548,275 and references cited therein. The antigen-anti-DC-SIGN antibody complex will bind to DC-SIGN and be taken up by and processed by the dendritic cells. It is proposed that binding to DC-SIGN on dendritic cells of just an antigen, rather than the complete pathogen, results in a positive immune response against the pathogen rather than the suppression of the immune response as is proposed to result when the complete pathogen binds to DC-SIGN and is taken up by dendritic cells.

Compounds that can be used in the compositions to inhibit binding of microorganisms in accordance with this disclosure include inhibitors for the C-type lectins known per se, including but not limited to those described in WO 93/01820 as mentioned above.

In general, these are compounds that can bind or adhere to, preferably in a reversible manner, or that can serve as a ligand for, the C-type lectins, in particular the C-type lectin DC-SIGN or natural variants or equivalents thereof. Examples are mannose carbohydrates such as mannan and D-mannose; fucose carbohydrates such as L-fucose; plant lectins such as concanavalin A; antibiotics such as pradimicin A; sugars such as N-acetyl-D-glucosamine and galactose; as well as suitable peptidomimetic compounds and small drug molecules, which can for instance be identified using phage display techniques. Furthermore, proteins such as gp120 and analogs or fragments thereof or similar proteins with binding capacity to C-type lectins on dendritic cells may be used, as well as isolated ICAM-receptors and analogs thereof, including parts or fragments thereof. Such parts or fragments should then preferably still be such that they can bind to the C-type lectins on the surface of dendritic cells or macrophages.

However, the use of carbohydrates is usually less desired from a therapeutic point of view, as they can be rapidly metabolized in vivo. Also, the use of plant lectins such as concanavalin A and pradimicin antibiotics can have disadvantages in a therapeutic setting, in particular when treating patients with autoimmune disorders and/or HIV infections.

Preferably, one or more physiologically tolerable and/or pharmaceutically acceptable compounds are used, such as defined in WO 93/01820. For instance, the use of gp120 or derivatives thereof may cause undesired side effects, in particular on the nervous system (vide WO 93/01820).

Therefore, according to particularly useful embodiments of the present disclosure, preferably an antibody directed against a C-type lectin as present/expressed on the surface of a dendritic cell, or a part, fragment or epitope thereof, is used. As used herein, the term antibodies includes inter alia polyclonal, monoclonal, chimeric and single chain antibodies, as well as fragments (e.g., Fab, F(ab')$_2$, F(ab'), Fv, Fd) and an Fab expression library. Furthermore, "humanized" antibodies may be used, for instance as described in WO 98/49306.

Such antibodies against the C-type lectins can be obtained as described hereinbelow or in any other manner known per se, such as those described in WO 95/32734, WO 96/23882, WO 98/02456, WO 98/41633 and/or WO 98/49306.

For instance, polyclonal antibodies can be obtained by immunizing a suitable host such as a goat, rabbit, sheep, rat, pig or mouse with a C-type lectin or an immunogenic portion, fragment or fusion thereof, optionally with the use of an immunogenic carrier (such as bovine serum albumin or keyhole limpet hemocyanin) and/or an adjuvant such as Freund's, saponin, ISCOM's, aluminum hydroxide or a similar mineral gel, or keyhole limpet hemocyanin or a similar surface active substance. After an immune response against the C-type lectin has been raised (usually within 1-7 days), the antibodies can be isolated from blood or serum taken from the immunized animal in a manner known per se, which optionally may involve a step of screening for an antibody with desired properties (i.e. specificity) using known immunoassay techniques, for which reference is again made to, for example, WO 96/23882.

Monoclonal antibodies may be produced using continuous cell lines in culture, including hybridoma and similar techniques, again essentially as described in the above cited references.

Fragments such as F(ab')$_2$ and Fab may be obtained by digestion of an antibody with pepsin or another protease and reducing disulfide-linkages and treatment with papain and a reducing agent, respectively. Fab-expression libraries may for instance be obtained by the method of Huse et al. (1989).

Preferably, a monoclonal antibody against the C-type lectin(s) on dendritic or macrophage cells is used, more specifically against DC-SIGN or an antigenic part thereof. Hereinbelow, the invention will be illustrated by means of monoclonals herein referred to as AZN-D1, AZN-D2, and AZN-D3 although similar monoclonals with comparable specificity for C-type lectins may also be used. Hybridomas that produce the monoclonals AZN-D1 and AZN-D2were deposited on Apr. 8, 1999 with the European Collection of Cell Cultures (ECACC), Centre for Applied Microbiology and Research, Porton Down, Salisbury, Wiltshire SP4 OJG, United Kingdom, under ECACC accession numbers 99040818 and 99040819,respectively. A hybridoma that produces AZN-D3 was deposited on Jul. 18, with the European Collection of Cell Cultures (ECACC), Centre for Applied Microbiology and Research, Porton Down, Salisbury, Wiltshire SP4 01G, United Kingdom, under ECACC accession number 03071801. Antibodies against the C-type lectins on dendritic cells, specifically against DC-SIGN, have been described by WO 00/63251.

For a further description of the methods and techniques known per se in which the antibodies of the invention can be used, reference is made to general textbooks, such as Sites et al., *Basic and clinical immunology* 8th Ed., Prentice-Hall (1994) and Roitt et al., *Immunology*, 2nd Ed., Churchill Livingstone (1994); both incorporated herein by reference. Particular reference is made to the general uses of antibodies and techniques involved therein as mentioned in sections 2.7 to 2.17 of the general reference work by Janeway-Travers, *Immunobiology, the immune system in health and disease*, Third Edition, which is incorporated herein by reference.

A composition of the invention may contain one or more of the above-mentioned active compounds. For instance, an anti-C-type lectin antibody can be formulated with mannose or fucose carbohydrates, lectins and/or antibiotics such as pradimicin A, whereby a synergistic effect may be obtained.

The present compositions may also contain or be used in combination with known co-inhibitory compounds, such as anti-LF3A; as well as other active principles known per se, depending upon the condition to be treated. For instance, the present compositions may be formulated or used in combination with immunosuppressants or immunomodulants.

Compositions in accordance with this disclosure can further be formulated using known carriers and/or adjuvants to provide a pharmaceutical form known per se, such as a tablet, capsule, powder, freeze dried preparation, solution for injection, etc., preferably in a unit dosage form. Such pharmaceutical forms, their use and administration (single or multi dosage form), as well as carriers, excipients, adjuvants and/or formulants for use therein, are generally known in the art and are for instance described in WO 93/01820, WO 95/32734, WO 96/23882, WO 98/02456, WO 98/41633 and/or WO 98/49306, all incorporated herein by reference. Furthermore, the formulation can be in the form of a liposome, as described in WO 93/01820.

Pharmaceutical formulations of antibodies, their administration and their use are generally described in WO 95/32734, WO 96/23882, WO 98/02456, WO 98/41633 and/or WO 98/49306.

The present compositions may further be packaged, for instance in vials, bottles, sachets, blisters, etc.; optionally with relevant patient information leaflets and/or instructions for use.

The compound or composition is in particular administered in such an amount that the interaction between DC-SIGN on dendritic cells and yeast or pathogen cells are altered or modified, more in particular in such an amount that the adhesion of dendritic cells to yeast or pathogen cells is reduced. Alternatively, the compound or composition in administered in such an amount that the interaction between DC-SIGN on dendritic cells and an antigen, e.g., a purified antigen, is enhanced.

In all the above methods and embodiments, the compounds/compositions used will be administered in a therapeutically effective amount, for which term reference is generally made to WO 93/01820, WO 95/32734 and/or WO 96/23882. The administration can be a single dose, but is preferably part of a multidose administration regimen carried out over one or more days, weeks or months.

All terms used herein have the normal meaning in the art, for which reference can be made to inter alia the definitions given in WO 93/01820, WO 95/32734, WO 96/23882, WO 98/02456, WO 98/41633 and/or WO 98/49306, analogously applied.

Furthermore, although the invention is described herein with respect to the specific 44 kDa C-type lectin receptor DC-SIGN, it is not excluded that other, generally similar C-type lectins, including natural variants of DC-SIGN, may also be present on dendritic cells and/or may be involved in dendritic cell/yeast (or other pathogen) cell interaction. Such variants will usually have a high degree of amino acid homology (more than 80% to more than 90%) with, and/or be functionally equivalent to DC-SIGN. Also, any such receptor will generally display properties similar to those as described herein; in particular that inhibition of this receptor, either by carbohydrate inhibitors or specific antibodies, will lead to an alteration of dendritic cell/yeast cell interaction.

The following Examples are offered by way of illustration and are not intended to limit the invention in any manner. Standard techniques well known in the art or the techniques specifically described below are utilized.

EXAMPLE 1

Reagents and Antibodies

Fluorescein isothiocyanate (FITC) was from Fluka. Mannan, D-mannose, and L-fucose were from Sigma Chemical Co. (St. Louis, Mo.). IL-4 and granulocyte macrophage colony stimulating factor (GM-CSF) used for culturing monocyte-derived dendritic cells were from Schering-Plough (International, Kenilworth, USA). The following Abs were used: AZN-D1,AZN-D2, AZN-D3 (IgG1, anti-DC-SIGN (Geijtenbeek et al., 2000a)); AZN-L50 (IgG1, anti-ALCAM) (Nelissen et al., 2000); NKI-L19 (IgG1 anti-$\beta_2$ integrins); mAB clone 19.2 against mannose receptor was from BD Biosciences PharmIngen. $\beta$-1,2-oligomannoside was isolated as described (Shibata et al., 1996; Shibata et al., 1985).

EXAMPLE 2

C. Albicans Culture Conditions

C. albicans, strain UC820, a clinical isolate that has been well described (Forsyth and Mathews, 1996), was maintained on agar slants at 4° C. Previous experiments showed that strain UC820 can develop hyphae and pseudohyphae in vitro and in vivo to the same extent as a panel of virulent control C. albicans. C. albicans UC820 was inoculated into 100 mL of Sabouraud broth and was cultured for 24 hours at 37° C. After 3 washes with pyrogen-free saline by centrifugation at 1500× g, the number of yeast cells was counted in a hemocytometer; occasional strings of 2 yeast were counted as 1 cfu of C. albicans. The suspension was diluted to the appropriate concentration with pyrogen-free saline. Microscopy confirmed that the suspension consisted of blastoconidia. When necessary, the blastoconidia were heat killed either at 56° C. for 1 hour or at 100° C. for 30 minutes.

EXAMPLE 3

Cells

Immature dendritic cells (imDC) were generated from human peripheral blood monocytes as described previously (Vissers et al., 2001). Briefly, monocytes were isolated by adherence to plastic and cultured in the presence of IL-4 (500 U/mL) and GM-CSF (800 U/mL) for 6-7 days. K562 transfectants either expressing DC-SIGN or ALCAM were generated by transfection of K562 cells with 10 µg of plasmid by electroporation as described previously (Geijtenbeek et al., 2000b; Nelissen et al., 2000). Positive cells were sorted several times to obtain stable transfectants with similar expression levels of DC-SIGN.

EXAMPLE 4

Immunofluorescence

Labeling of *Candida* cells was performed as follows: viable or heat killed (60 minutes at 56° C. or 30 minutes at 100° C.) yeast cells were resuspended to $2 \times 10^8$/mL in 0.1 mg/mL FITC in 0.05 M carbonate-bicarbonate buffer (pH 9.5). After incubation for 15 minutes at room temperature in the dark, FITC-labeled *Candida* cells were washed twice in PBS containing 1% BSA (PBA buffer) and analyzed by flow cytometry.

DC or K562 were stained in PBA with primary Abs and FITC-conjugated secondary Abs and were analyzed by flow cytometry using the FACScalibur (BD Biosciences, Mountain View, Calif.). Isotype-specific controls were included.

EXAMPLE 5

*Candida* Binding Studies

DC or K562 transfected cells were stained with anti-CD45-APC prior to exposure to FITC labeled live or heat inactivated *Candida*. DC or K562 cells expressing DC-SIGN or ALCAM (control) were or were not preincubated for 10 minutes at room temperature with mannan (300 µg/mL), mannose (100 mM), facose (100 mM), EGTA (5 mM), or a mixture of AZN-D1 and AZN-D3 (20 µg/mL), in 20 mM Tris pH 8.0, containing 150 mM NaCl, 1 mM $CaCl_2$, 2 mM $MgCl_2$, and 1% BSA (TSA buffer) or, when EGTA was used, in PBS. Subsequently, FITC labeled *Candida* were resuspended to the appropriate concentrations either in TSA or PBS and added in various cell/*C. albicans* ratios. After incubation, cell-*Candida* conjugates were analyzed by flow cytometry, and the relative difference in mean fluorescence intensity of the double labeled events compared with that of control cells was calculated. Cells were labeled with anti-CD45APC to discriminate cells binding FITC-labeled yeast particles from yeast aggregates.

EXAMPLE 6

Fluorescent Beads Adhesion Assay

The fluorescent beads adhesion assay was performed as described earlier (Geijtenbeek et al., 1999; Nelissen et al., 2000). Briefly, carboxylate-modified TransFluorSpheres (488/645 nm, 1.0 μm; Molecular Probes, Eugene, Oreg.) were coated with ICAM-3-Fc or ALCAM-Fc, and adhesion was determined by measuring the percentage of cells that have bound fluorescent beads by flow cytometry. In inhibition studies, the bead adhesion assay was performed in the presence of 0.3 mg/mL mannan, 5 mM EGTA, or 20 μg/mL antibodies against DC-SIGN or ALCAM.

EXAMPLE 7

Phagocytosis

Immature DC ($5 \times 10^5$) were incubated with unopsonized live FITC-labeled *Candida* cells ($2.5 \times 10^6$) in a total volume of 500 μL at 37° C. in a water bath with orbital shaking at 150 rpm for various periods of time. At the end of the incubation period, the DC binding *Candida* are separated from unbound *Candida* by a Ficoll gradient.

The samples were then adhered on poly-L-lysine coated glass coverslips, fixed in 1% paraformaldehyde in PBS for 15 minutes at room temperature, and permeabilized in cold methanol for 5 minutes on ice. After a blocking step in PBS/3% BSA for 60 minutes at room temperature, cells were labeled with mAb (10 μg/mL in PBS/3% BSA) for 60 minutes at room temperature and subsequently incubated with Cy5-conjugated Goat-anti-Mouse F(ab')$_2$ fragments for 30 minutes at room temperature. Finally, the anti-bleach reagent Mowiol was added, and samples were analyzed using a MRC1024 confocal microscope (Bio-Rad).

EXAMPLE 8

*Candida Albicans* is a Ligand of Dendritic Cell Specific ICAM-3 Grabbing Non-integrin (DC-SIGN)

The erythroleukemic cell line K562 transfectants stably expressing DC-SIGN (K-SIGN) (Geijtenbeek et al., 2000a) were used to investigate the potential of *C. albicans* to bind DC-SIGN in the absence of any other known *C. albicans*, receptors. Binding to ICAM-3 fluorescent beads was used as a positive control for DC-SIGN function. K562 cells transfected with the homotypic Activated Leukocyte Cell Adhesion Molecule ALCAM (Nelissen et al., 2000) (K-ALCAM), which is expressed by DC but does not bind any of the known ligands of DC-SIGN, were used as negative control. The monoclonal antibodies AZN-D1 and AZN-L50 were used to detect DC-SIGN and ALCAM, respectively. The K562 transfectants stably express DC-SIGN and ALCAM, (FIGS. 1A-1 through 1A-3) with expression levels similar to that observed previously (Geijtenbeek et al., 2000a; Nelissen et al., 2000).

Transfectant cells were labeled with CD45APC to discriminate cells binding FITC labeled yeast from yeast aggregates. Results from a representative experiment are shown in FIG. 1B. DC-SIGN clearly mediated adhesion to both *C. albicans* and ICAM-3-Fc-coated beads. K-ALCAM cells, which are able to bind only ALCAM-Fc beads, were used as negative control.

Figure 1C:
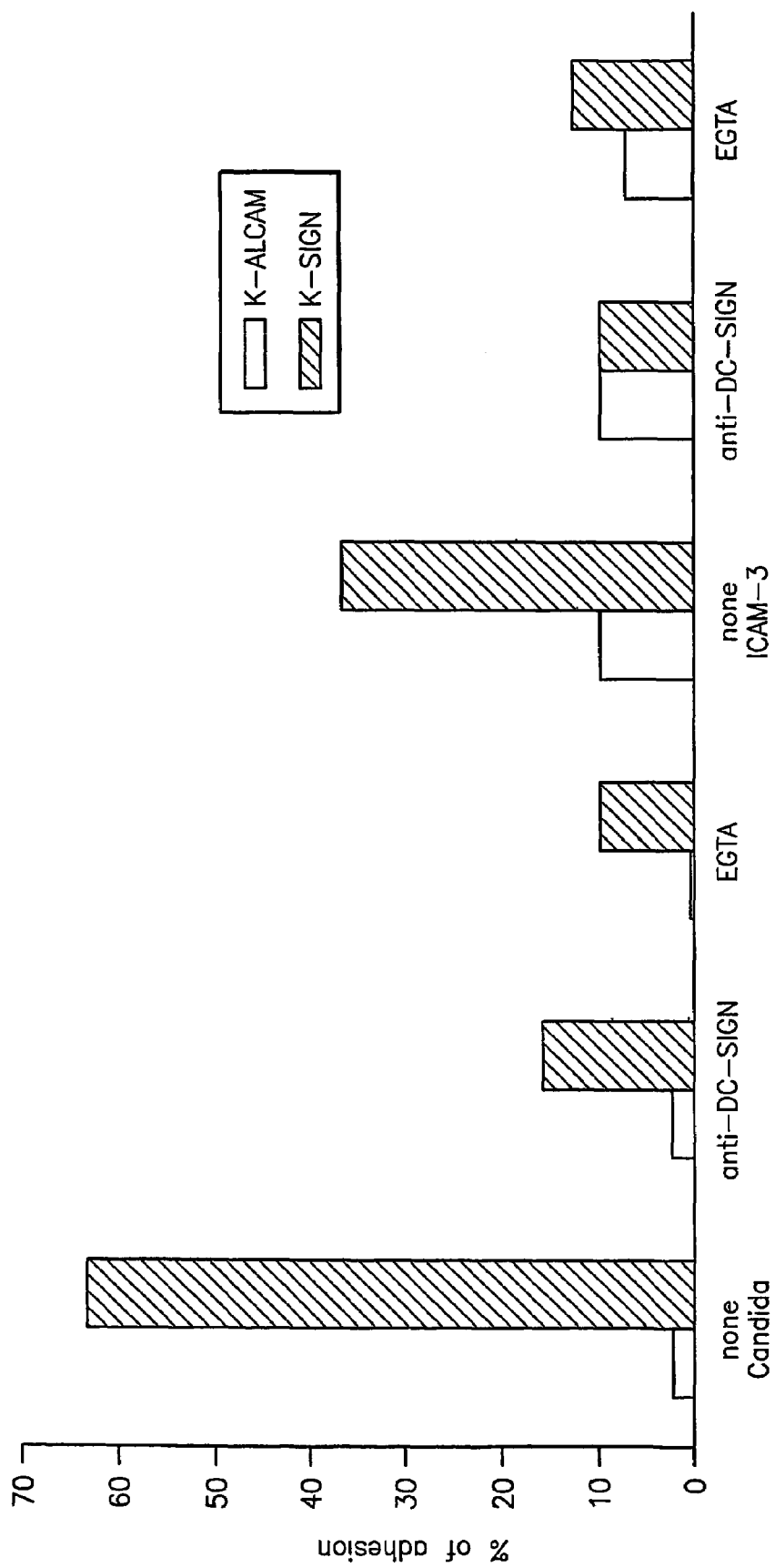
Figure 1D:
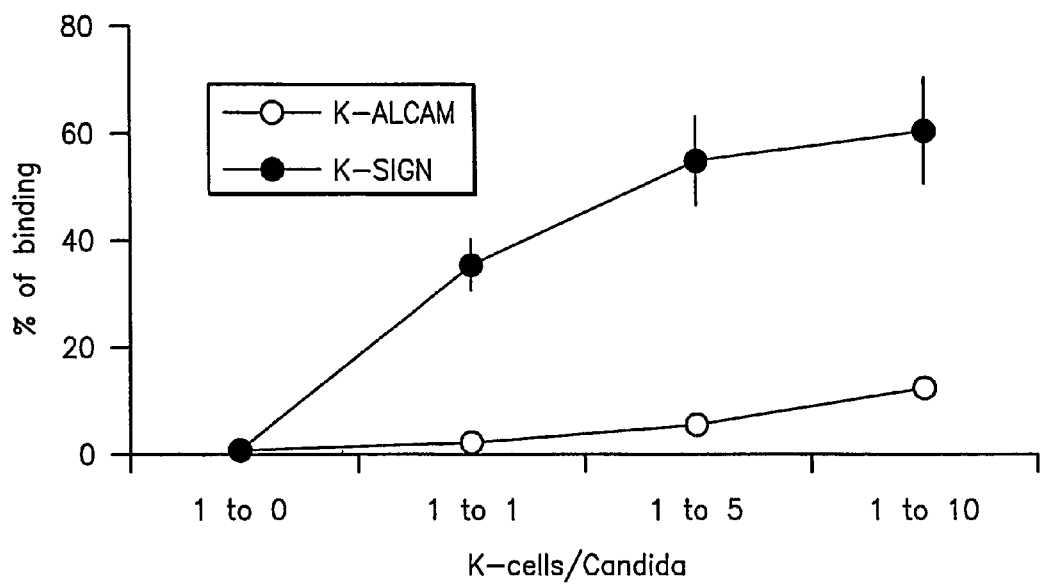
Figure 1E:
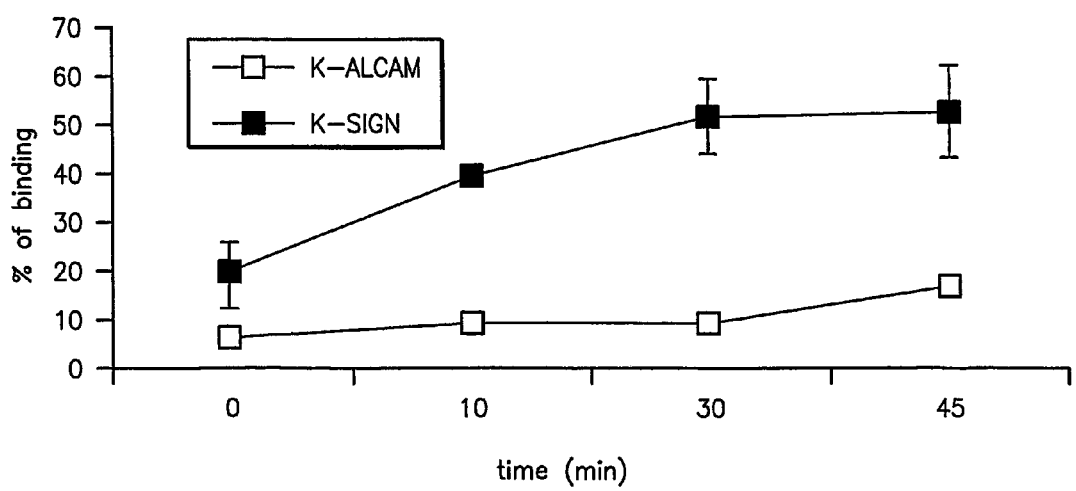

*C. albicans* and ICAM-3 specific adhesion was determined in the presence of blocking anti-DC-SIGN (AZN-D1) mAB (20 μg/mL). Binding of *C. albicans* by K -SIGN is significantly inhibited by blocking antibodies against DC-SIGN; in addition, the calcium chelator EGTA (present at 5 mM) abrogates binding (FIG. 1C). This $Ca^{2+}$ dependence confirms that binding to *C. albicans* is mediated by the C-type lectin domain of DC-SIGN. Depending on the concentration of *C. albicans* (FIG. 1D) and on the incubation time (FIG. 1E), binding of K -SIGN to the yeast cells increases significantly.

Figure 1F:
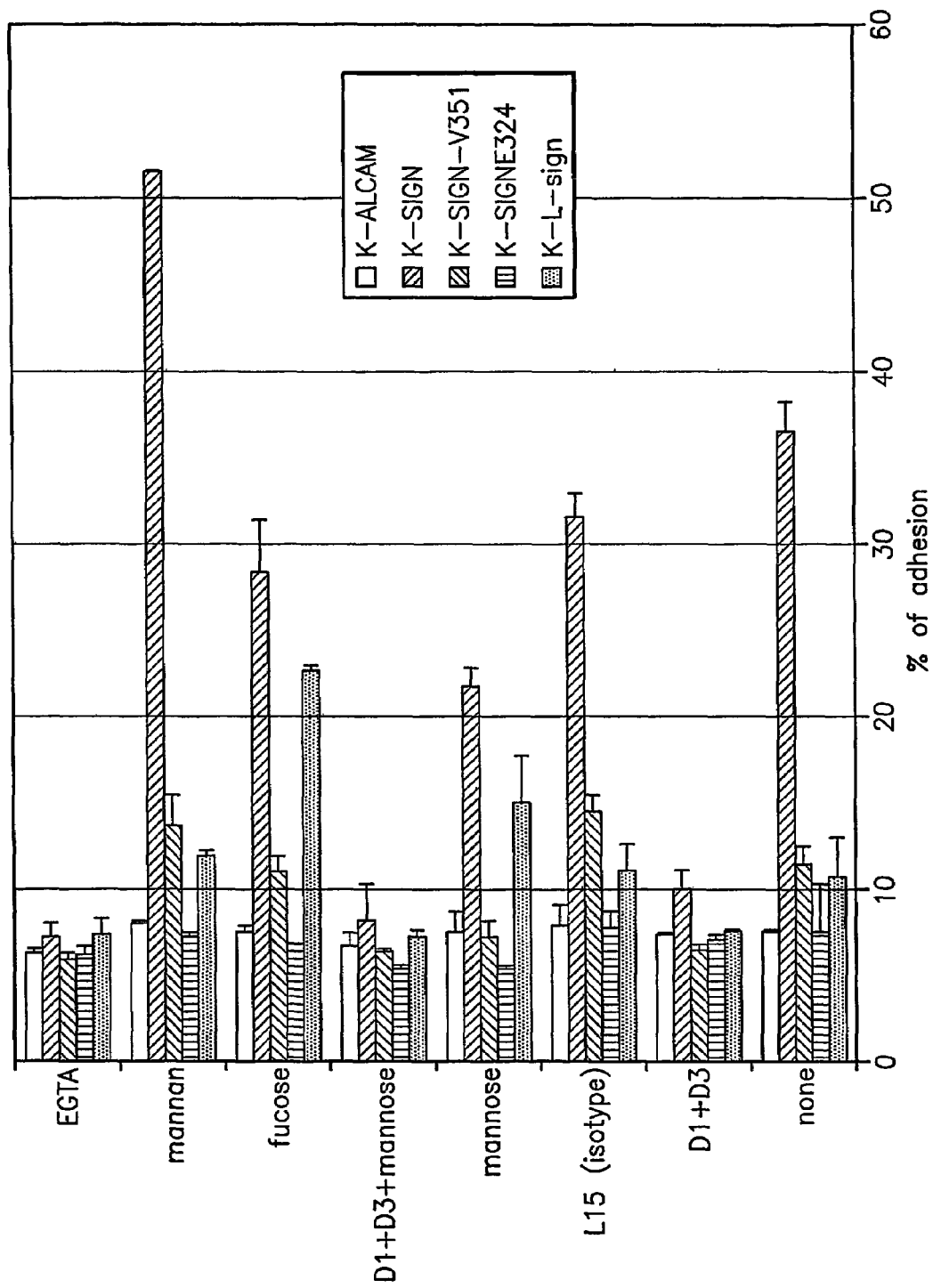

Additional studies were performed to determine the effect on binding of *C. albicans* to K562 transfectants. FIG. 1F shows results for K562 cells transfected with K-ALCAM, K-SIGN, K-SIGN-V351 (K562 transfected with DC-SIGN with a mutation of valine to glycine at amino acid 351), K-SIGNE324 (K562 transfected with DC-SIGN with a mutation of glutamic acid to glutamine at amino acid 324), and D-L-SIGN (K562 transfected with L-SIGN (see WO 02/50119 or GenBank Accession No. AF290887 for sequence of L-SIGN that is a protein related to DC-SIGN)). Binding of *C. albicans* to each of these cells was performed in the presence of either: no blocker, AZN-D1+AZN-D3 antibodies, L15 (an antibody isotypic for AZN-D1 and AZN-D3), mannose, AZN-D1+AZN-D3+mannose, fucose, mannan, or EGTA. The results indicate binding of *Candida* to K562 cells transfected with wild-type DC-SIGN. Binding was not seen to either mutated form of DC-SIGN, to L-SIGN or to ALCAM. Incubation in the presence of AZN-D1+AZN-D3 greatly inhibited this binding. EGTA also prevented the binding. The presence of either mannose or fucose resulted in some inhibition of binding of *C. albicans* to the K562 cells transfected with wild-type DC-SIGN. A control experiment using an antibody isotypic to AZN-D1 and to AZN-D3 showed only a minor effect.

Figures 1, 4A:
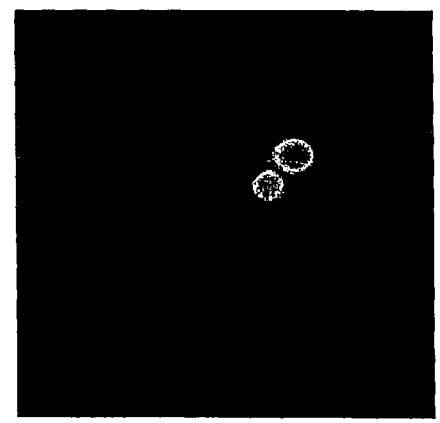
Figures 2, 4A:
Figures 3, 4A:
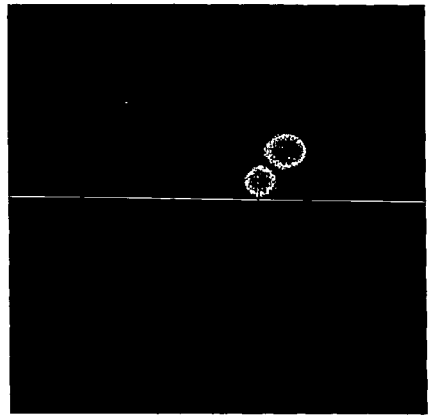
Figures 4, 4A:
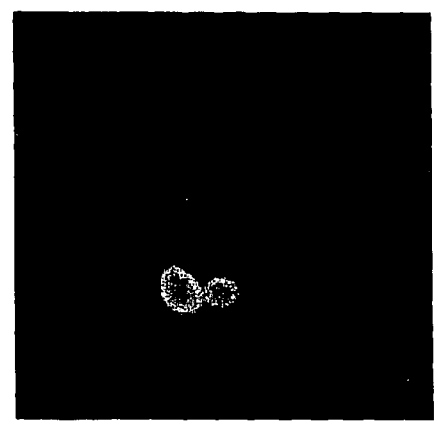
Figures 4, 4A, 5:
Figures 4, 4A, 5, 6:
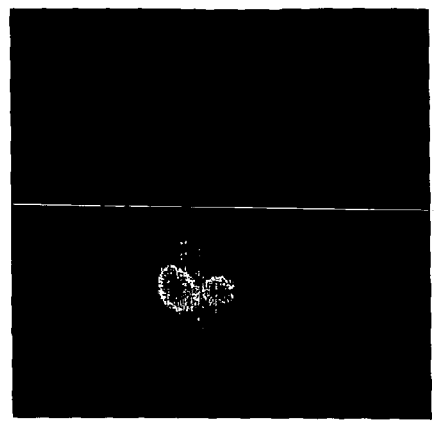
Figure 7:
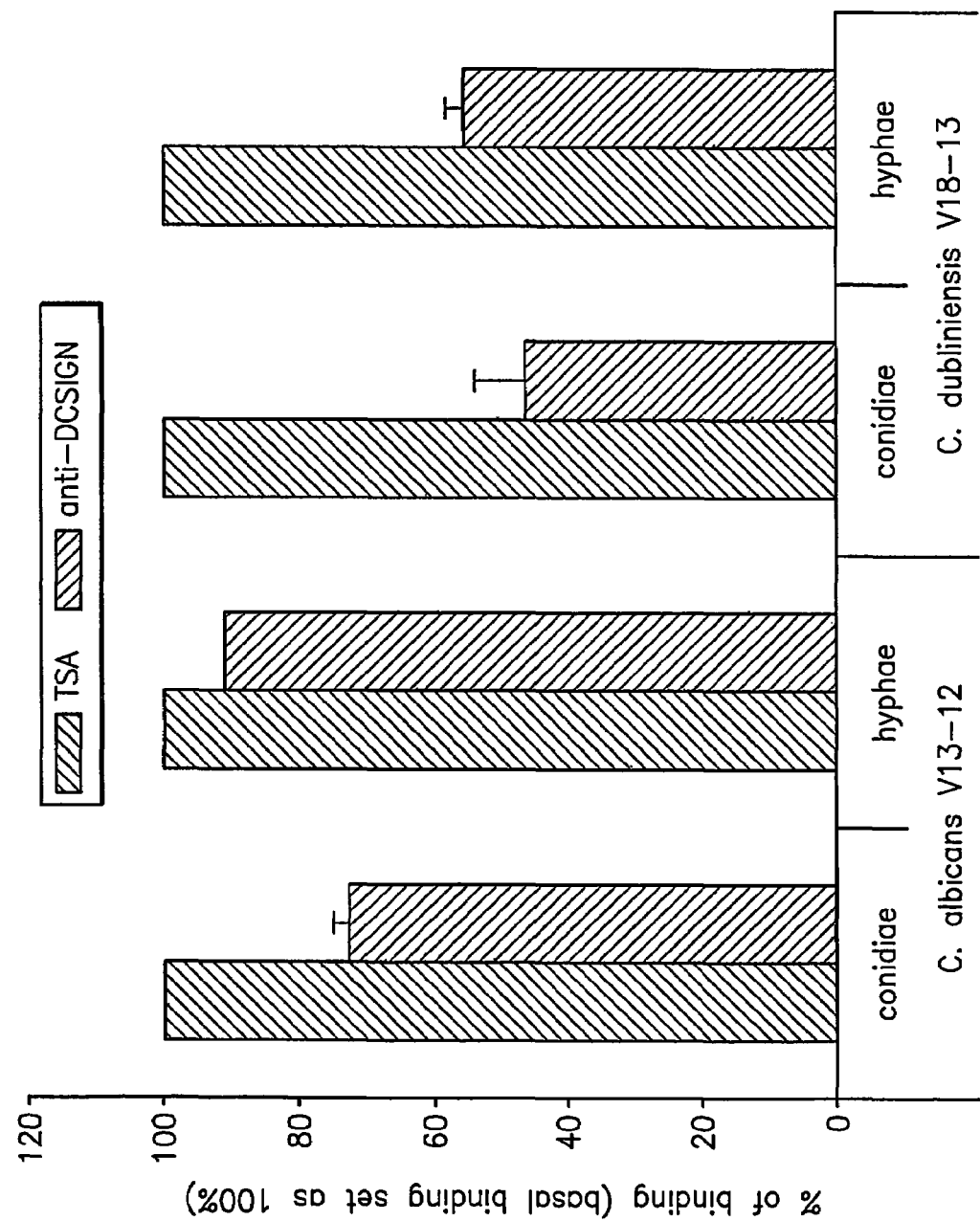
FIG. 7 shows the contribution of DC-SIGN to binding of *C. albicans* and *C. dubliniensis* on immature dendritic cells.

Further studies were performed as above but using other strains or species of yeast and also comparing binding of the conidiae versus binding of the hyphal form of the organism. FIG. 6 shows the binding to K-SIGN cells of conidiae and hyphae of *C. albicans* strains V13-12, V15-31 and V18-17 and *C. dubliniensis* strains V18-13, 4247 and 3588. These are clinical strains isolated from patients. It is seen that the conidiae or single-celled form of the yeast bind to DC-SIGN better than do the hyphae. The binding of each form to K-SIGN cells is inhibited by anti-DC-SIGN antibody and by EGTA (FIG. 6). FIG. 7 is a different representation of the effect of anti-DC-SIGN antibody on binding of each of live conidiae and hyphae to immature dendritic cells for each of *C. albicans* and to *C. dubliniensis*. In each case the binding in buffer alone in the absence of antibody was set as 100%. This shows that anti-DC-SIGN has a small but real inhibition of binding of the two species for both conidiae and hyphal forms. Much of the binding to the immature dendritic cells is to mannose receptors, which binding is not affected by the anti-DC-SIGN antibody.

FIGS. 8A-F show the binding of various species of *Candida* as well as *Aspergillus fumigatus* to K-SIGN cells. The amount of binding varies between the species, but in all cases, except possibly *C. tropicalis* and *C. parapsilosis* which each had very low binding, the binding is inhibited by anti-DC-SIGN and by EDTA. This was true for both the conidiae and hyphae (no data for *C. glabrata* for hyphae).

EXAMPLE 9

DC-SIGN Binds Live and Heat Inactivated Yeast Forms of *Candida Albicans*

Figure 2:
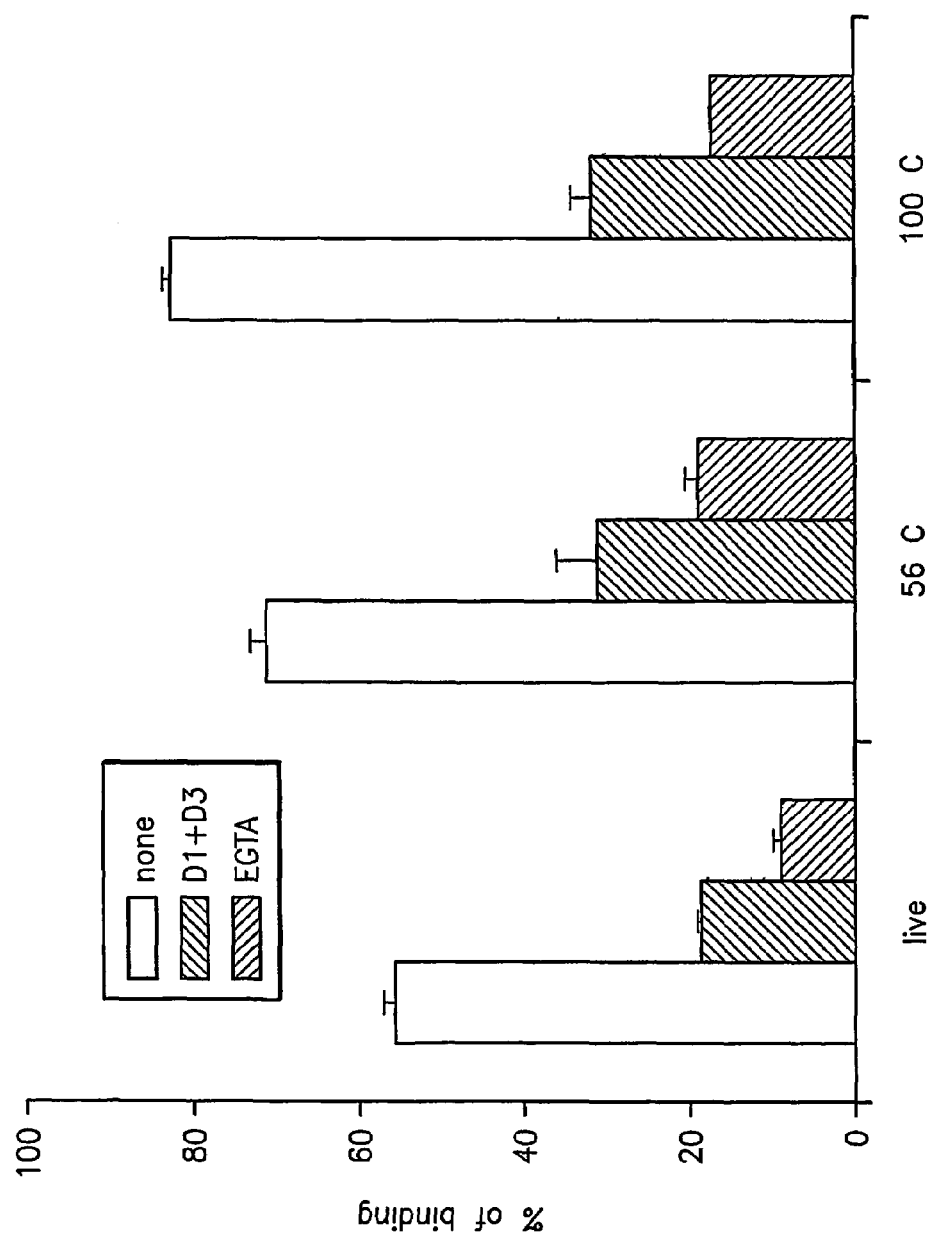

In various experiments, heat inactivated *C. albicans* were used instead of live cells. In order to exclude the possibility that the binding of DC-SIGN to heat-inactivated *C. albicans* was due to artifacts derived from the heat treatment, K-SIGN were allowed to interact with both live and heat-inactivated *C. albicans* yeast. As shown in FIG. 2, the percentage of binding did not increase significantly upon heat inactivation, when compared with binding to live yeast cells. In addition, the blocking of binding by using Ab against DC-SIGN is also not profoundly altered by heat treatment. However, in similar experiments using *C. dubliniensis* it was found that heat killing the yeast changed the binding affinity, the heat killing resulting in a dramatic decrease in the binding of the single celled yeast form from about 47% to about 10%.

EXAMPLE 10

Monocyte-derived DC Bind *C. Albicans* Also Through DC-SIGN

DC are specialized in binding and uptake of antigen. (Sallusto et al., 1995), and recently it has been published that the interaction between DC and *Candida* is mediated by the mannose-fucose receptor (d'Ostiani et al., 2000; Newman and Holly, 2001). However, considering the present findings on K-SIGN and the observation that *C. albicans* can be found in areas of the body (sub-mucosa) highly enriched in DC-SIGN positive cells, the contribution of DC-SIGN on immature DC in binding *Candida* was further investigated by the present work.

Figure 3A:
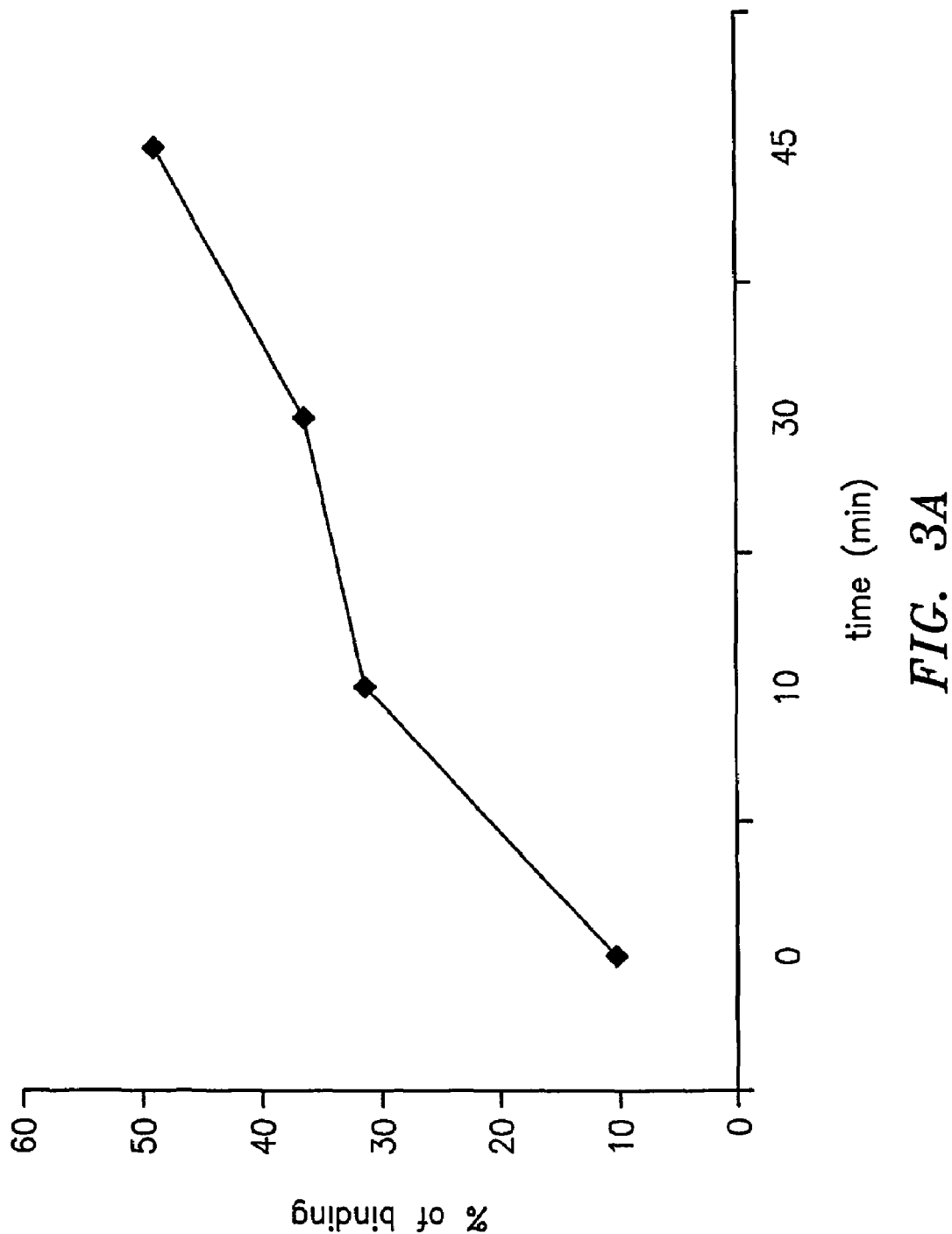
FIG. 3A shows that dendritic cells bind *C. albicans* through DC-SIGN and that the binding of immature dendritic cells (imDC) to *C. albicans* increases with time.

In FIG. 3A it is shown that human monocyte-derived immature DC are able to bind *C. albicans*, and that this interaction increases with time. For this experiment $50 \times 10^3$ dendritic cells were incubated with heat inactivated *Candida* ($500 \times 10^3$). This is in agreement with published results that DC are able to internalize *C. albicans* within 10-20 minutes of incubation at 37° C., reaching a maximum after 60 minutes (d'Ostiani et al., 2000; Newman and Holly, 2001).

Figure 3B:
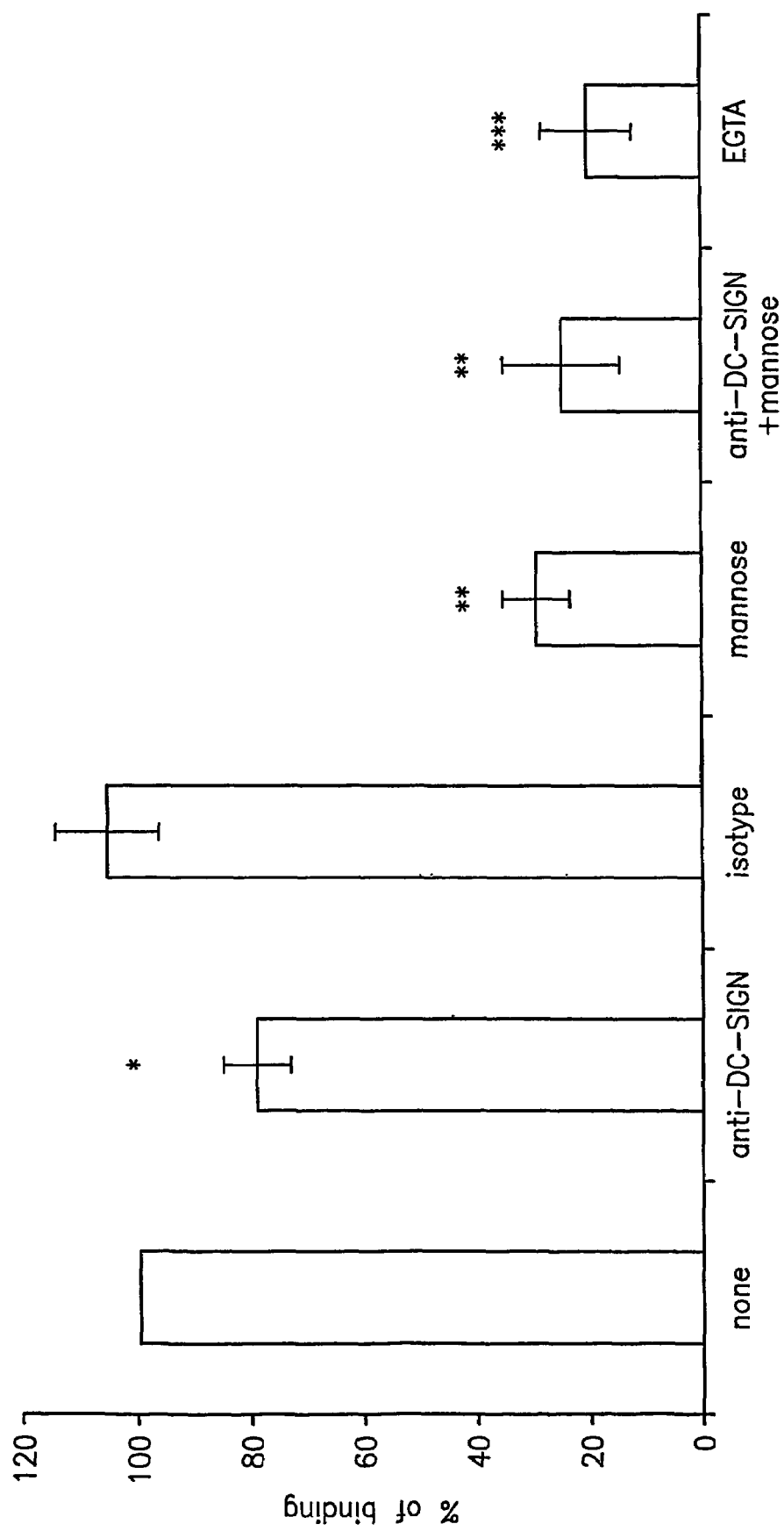
FIG. 3B shows results illustrating the relative contribution of DC-SIGN and mannose receptors in the binding of *Candida*. The binding of immature monocyte-derived DC to *C. albicans* in the presence of blocking agents is shown.

In an attempt to establish the contribution of both the mannose receptor and DC-SIGN, immature DC were incubated with specific inhibitors before interacting with *C. albicans*. Immature monocyte derived dendritic cells ($50 \times 10^3$), which were CD45APC labeled, were incubated with heat-inactivated *Candida* ($500 \times 10^3$) in the absence or presence of AZN-D1 and AZN-D3, anti-DC-SIGN mAb (20 µg/mL each), mannose (100 mM), and EGTA (5 mM). The results (an average of five independent experiments) are shown in FIG. 3B. The binding to *C. albicans* in the absence of inhibitors was set as 100%. * indicates P<0.01 and ** indicates P<0.001 percentage of binding in the presence of blocking agent vs. percentage of binding in the absence of blocking agent. The results show that antibodies against DC-SIGN block binding, though partially (about 20%) and to a minor extent with respect to the blocking exerted by mannose on the MR (about 60-70%). The combination of both anti-DC-SIGN Abs and mannose increases blocking up to about 80-85%. The observation that EGTA is the most effective blocking agent corroborates the finding that indeed C-type lectins are primarily involved in the binding of *C. albicans* on immature DC. The bar labeled "isotype" in FIG. 3B is a control incubation including an irrelevant isotypic antibody, the results indicating that inhibition of binding by anti-DC-SIGN is due to the specificity of the AZN-D1 and AZN-D3 antibodies rather than to the isotype of the anti-DC-SIGN antibodies.

Experiments were performed to measure the amount of each of DC-SIGN and mannose receptor on the surface of immature dendritic cells. The cells were incubated with antibody (AZN-D1) against DC-SIGN or with antibody against the mannose receptor. Both antibodies stain the same number of cells with approximately the same intensity. These results are shown in FIGS. 3C-1 and 3C-2. The results show that both receptors (DC-SIGN and the mannose receptor) are present in equal quantities on the surface of dendritic cells.

Figure 3D:
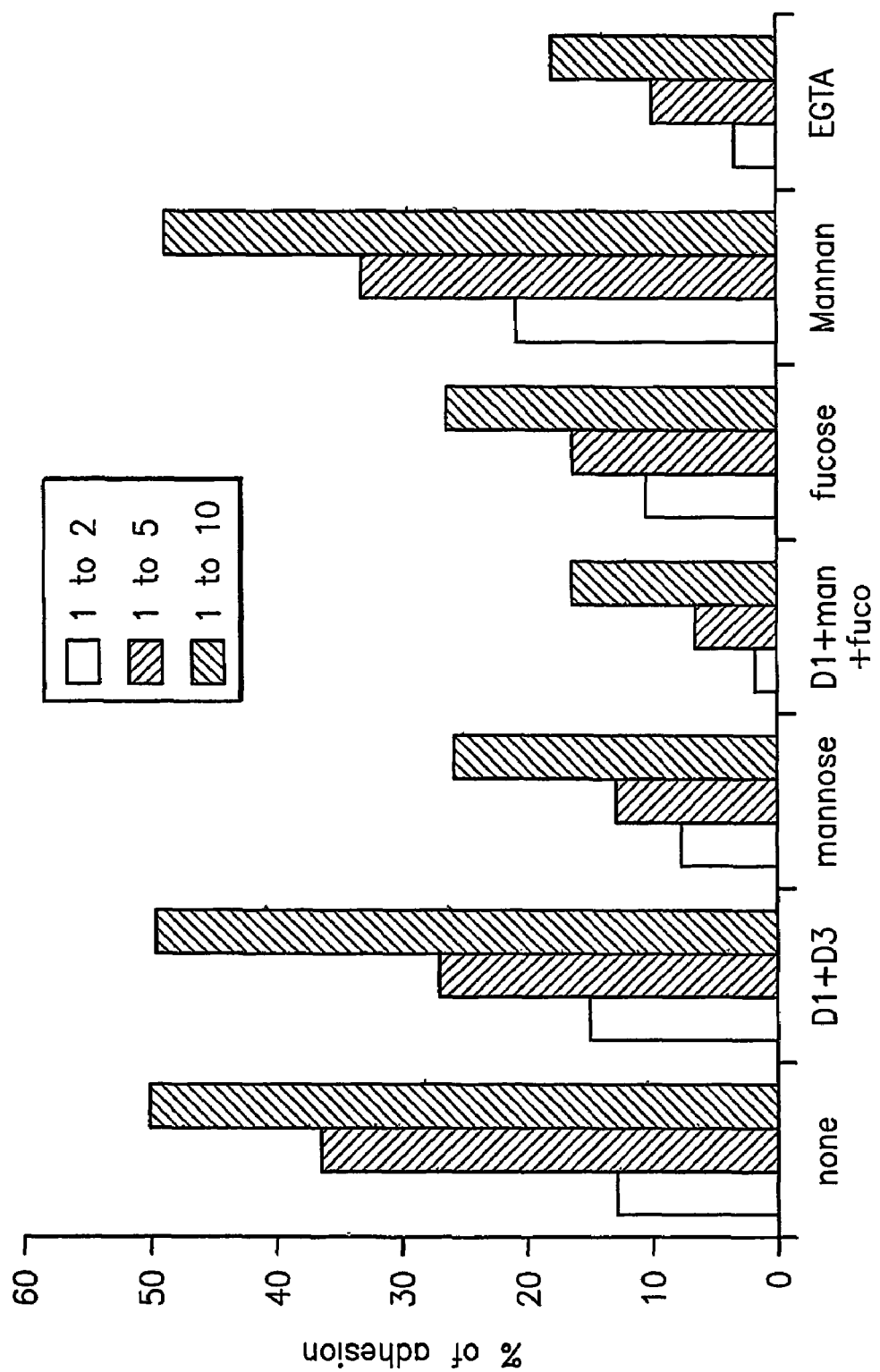
FIG. 3D shows binding of *C. albicans* to immature dendritic cells at various ratios of dendritic cells to *C. albicans* and in the presence of various inhibitors of binding.

Additional studies were performed showing the effect on binding of increasing the ratio of *Candida* to immature dendritic cells and the ability of various agents to inhibit this binding. The results are shown in FIG. 3D. Immature dendritic cells and *C. albicans* were mixed at ratios of 1:2, 1:5 and 1:10. It is seen that binding increases as the ratio of *Candida* to imDC increases. It is further seen that the antibodies AZN-D1 and AZN-D3 can only partially inhibit the binding of *Candida* to imDC. Mannose and fucose each have greater inhibitory effects on binding than do the anti-DC-SIGN antibodies; the combination of antibodies, mannose and fucose has the greatest inhibitory effect. Mannan did not block the binding, whereas EGTA largely eliminated binding.

In addition to DC-SIGN and the MR, DC are known to express high levels of the $\beta_2$-integrin MAC1, which has already been implicated in the binding of lymphocytes to *C. albicans* (Forsyth et al., 1998). Nevertheless, no blocking of *C. albicans* binding was detected when anti-$\beta_2$-integrin antibody (NKI-L19) was used, suggesting that MAC-1 is not likely involved in *C. albicans* binding on human immature monocyte derived DC. Moreover, the use of laminarin to interfere with the interaction between the DC specific C-type lectin Dectin-1 and *C. albicans* did not show any block either. These observations strongly suggest that on immature DC the binding of *C. albicans* is due to a greater extent to MR and also to a lesser extent to DC -SIGN.

EXAMPLE 11

DC-SIGN Phagocytoses *Candida Albicans*

Figures 1, 4B:
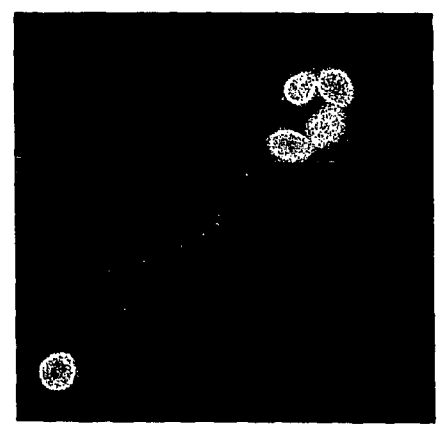
Figures 2, 4B:
Figures 3, 4B:
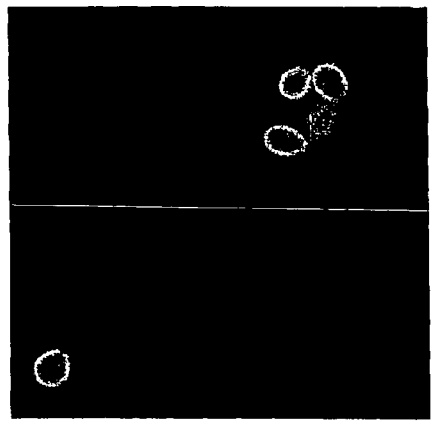
Figures 4, 4B:
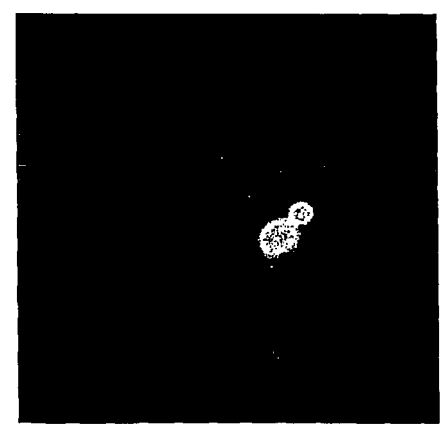
Figures 4, 4B, 5:
Figures 4, 4B, 5, 6:
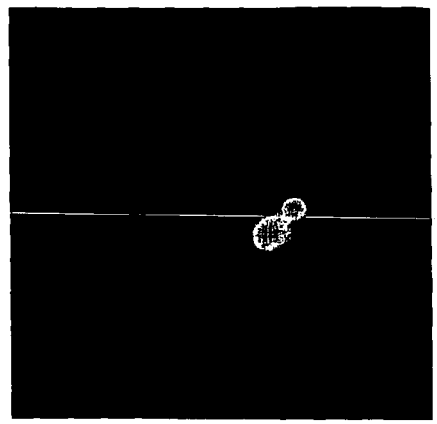

It was recently shown that DC-SIGN is an antigen uptake receptor, facilitating phagocytosis within minutes (Engering et al., 2002). In order to determine whether DC-SIGN contributes also to the internalization of *C. albicans* by immature DC, experiments were performed allowing DC to interact with FITC-labeled *Candida* for 60 minutes at 37° C. to allow phagocytosis. Subsequently, the DC were fixed, permeabilized and fluorescently labeled with specific Abs against various receptors. Confocal microscopy images (FIGS. 4A-E) of immature DC show that binding of FITC labeled *C. albicans* (green) co-localizes (merged) with Cy5 labeled DC-SIGN (blue). Labeling of $\beta_2$ integrins (NKI-L19), ALCAM (NKI -L50) and mannose receptor was used as controls. FIGS. 4A and 4B represent labeling of the $\beta_2$-integrin MAC-1 and ALCAM, respectively; labeling of these receptors was used as negative control, since they were shown not to be involved in the binding of *Candida* by DC. As expected, none of these adhesion receptors was detectable in vesicles containing *Candida*.

Figure 4D:
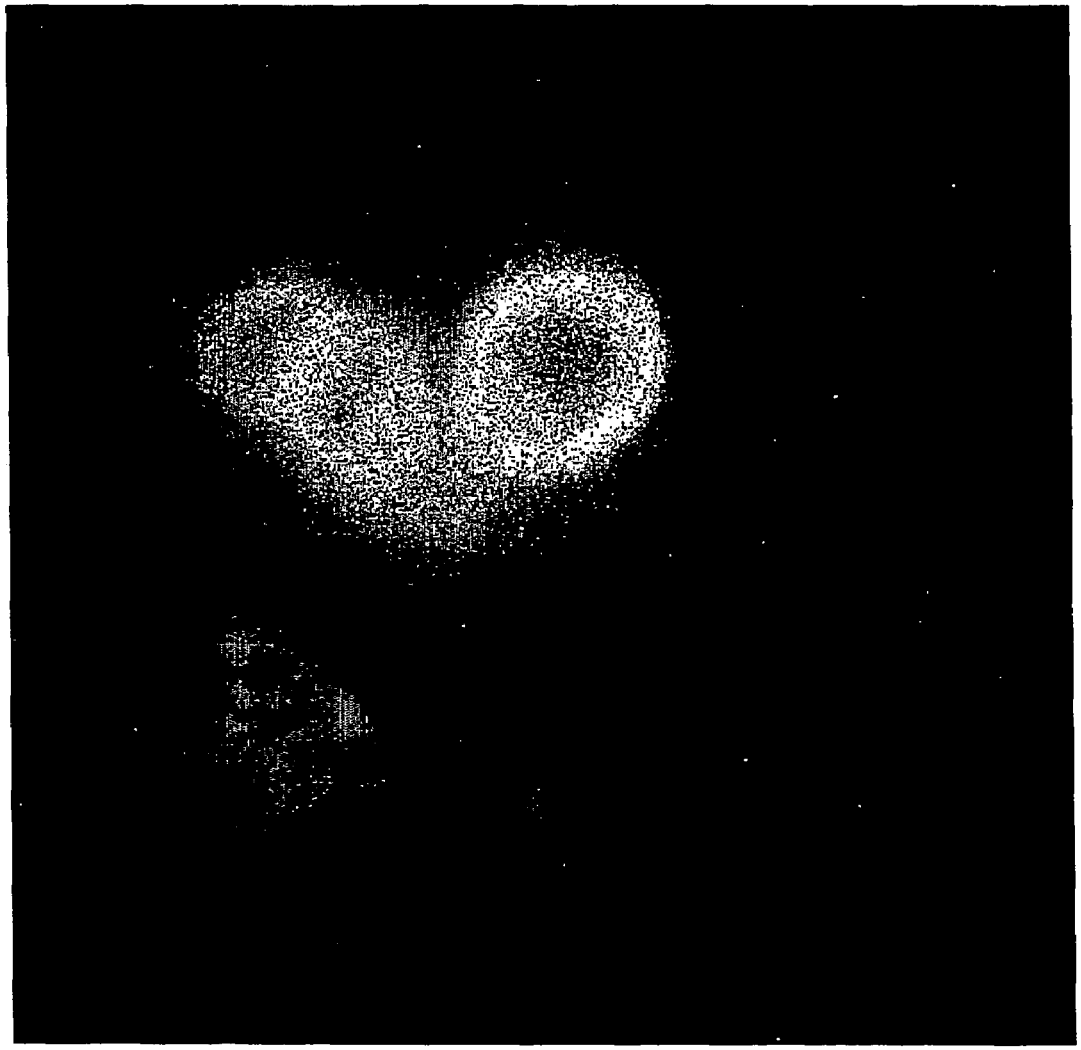
Figure 4E:
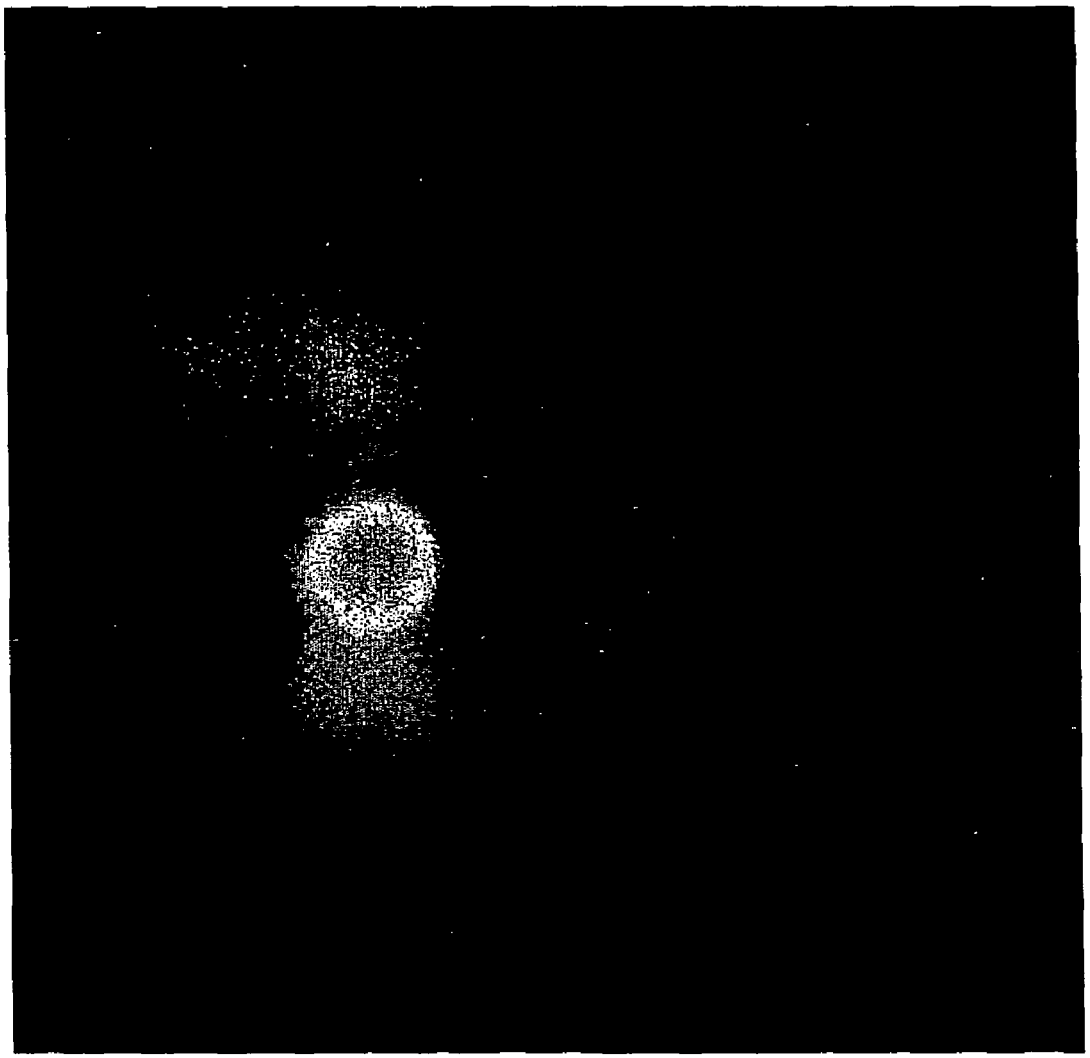
Figure 5:
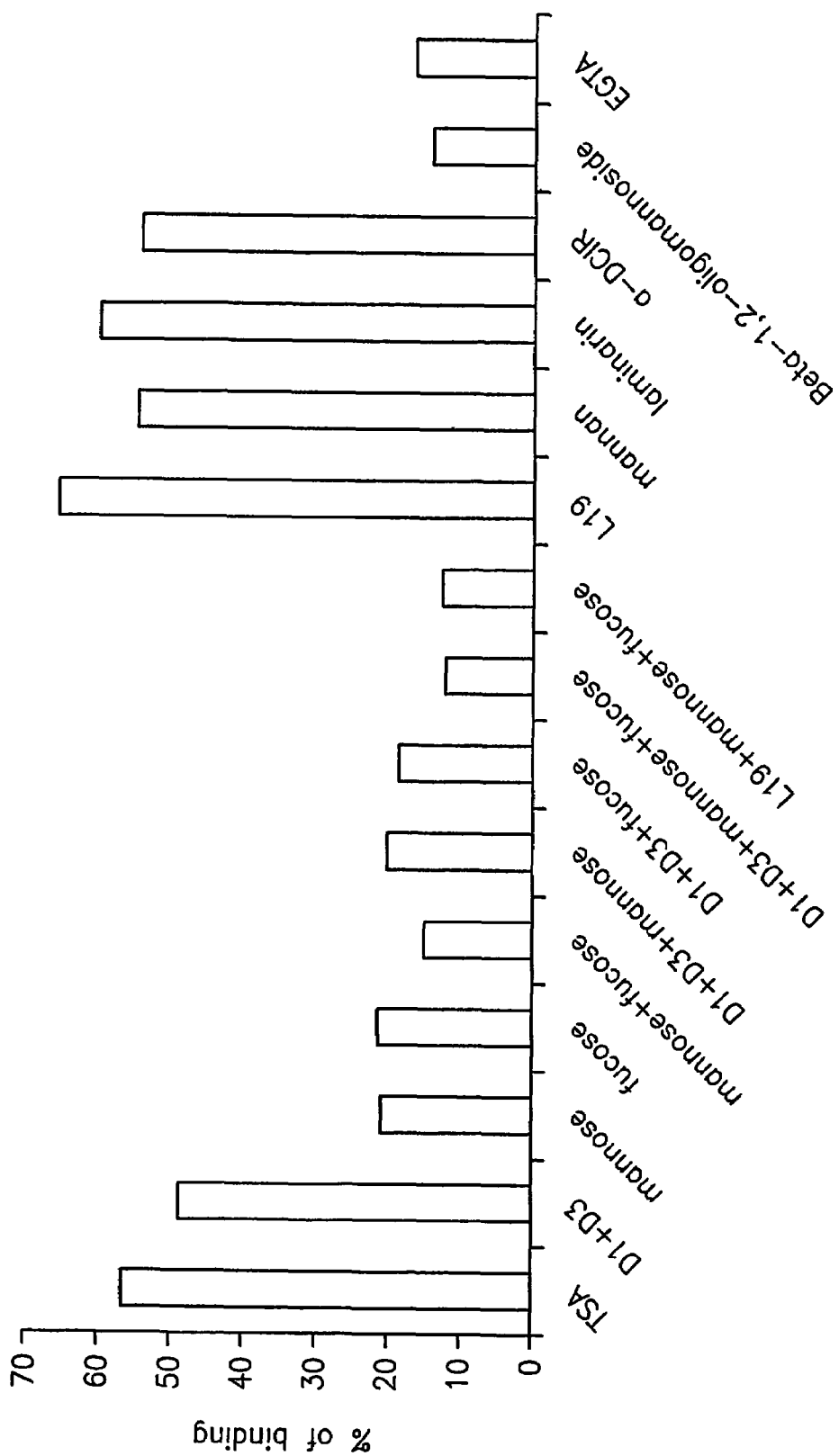
Figure 6:
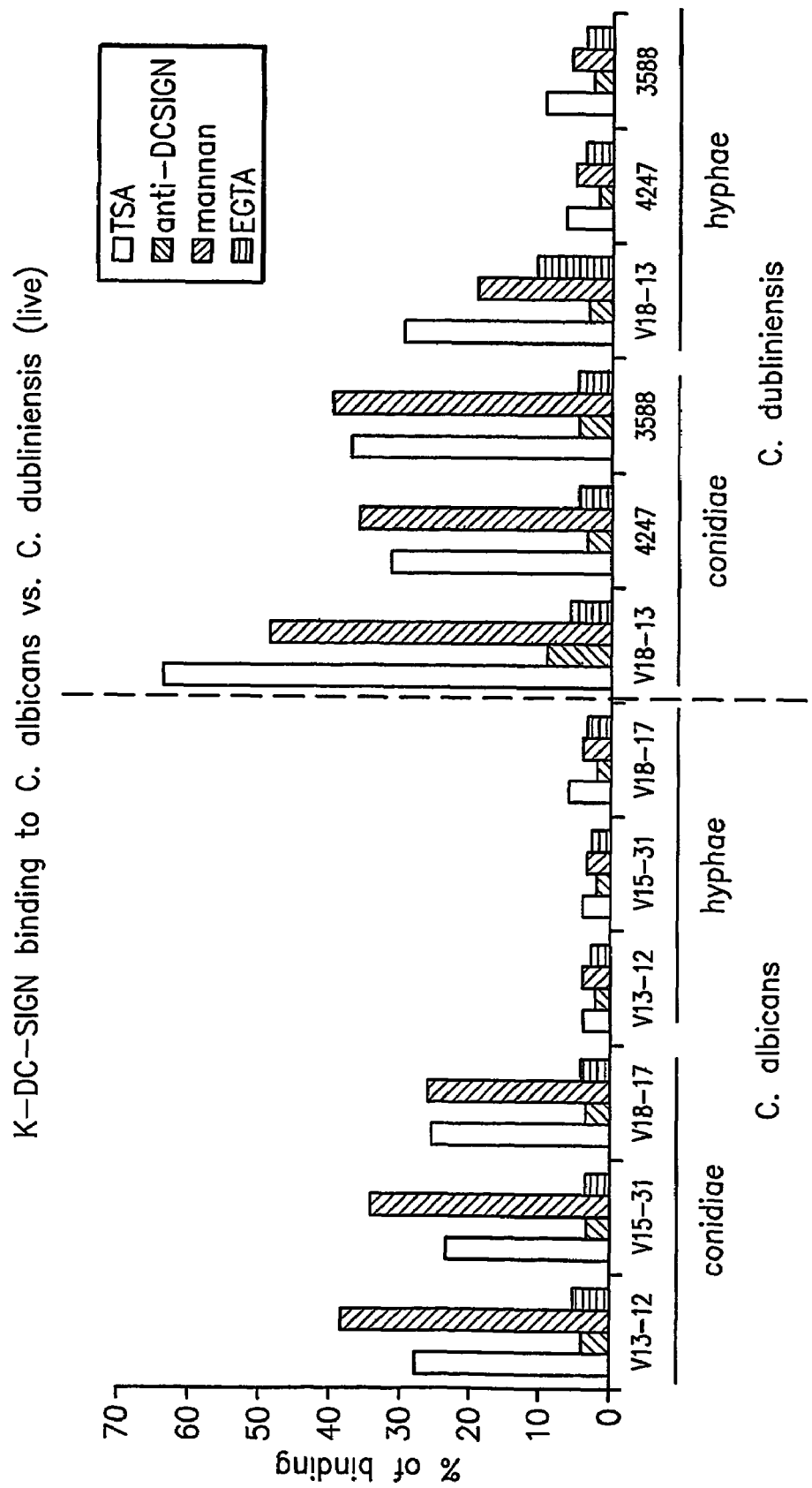

In contrast, FIG. 4C clearly shows colocalization of DC-SIGN with some of the internalized *Candida*, indicating the involvement of this lectin in binding and uptake of this pathogen. The fact that the majority of vesicles do not seem to contain DC-SIGN is explained by the primary role of MR in the phagocytosis of *C. albicans*. In fact, as shown in FIG. 4D, a great colocalization between MR and ingested *Candida* was observed. In order to determine whether DC-SIGN was able to internalize *Candida* also in presence of inhibitors of MR, DC were allowed to phagocytose *Candida* in the presence of mannose. As shown in FIG. 4E, vesicles containing DC-SIGN colocalizing with FITC-labeled *Candida* could still be clearly observed despite the presence of mannose. The presence of EGTA almost completely blocked phagocytosis.

EXAMPLE 12

DC-SIGN Binds β-1,2-Linked Oligomannoside

Binding of *C. albicans* to immature dendritic cells was performed in the presence of numerous possible inhibitors of binding. The results are shown in FIG. 5. Binding was performed in the presence of buffer (TSA), anti-DC-SIGN antibodies AZN-D1+AZN-D3, mannose, fucose, mannose+fucose, AZN-D1+AZN-D3+mannose, AZN-D1+AZN -D3+ fucose, AZN-D1+AZN-D3+mannose+fucose, NKI-L19 (an IgG1 anti-β$_2$-integrin)+mannose+fucose, NKI-L19, mannan, laminarin (a β-1,3-linked oligomannoside), antibody to DCIR (a C-type lectin, see Bates et al. (1999)), β-1,2-oligomannoside, and EGTA.

As seen above, the AZN-D1 and AZN-D3 inhibited the imDC/*Candida* binding to only a small extent. Also, L19, mannan, laminarin and anti-DCIR had only minor effects upon the binding. Mannose and fucose inhibited binding to a large degree as did EGTA. Additionally, it was found that β-1,2-oligomannoside greatly inhibited binding, contrasting with the lack of inhibition by laminarin. This indicates that binding between DC-SIGN and *Candida* occurs via the β-1, 2-oligomannoside on *C. albicans*.

Additional experiments will test the ability of an anti-*Candida* monoclonal antibody that binds to β-1,2-oligomannoside to block the binding of *C. albicans* to DC-SIGN bearing cells. Furthermore, a peptidomimetic (FHENWPS (SEQ ID NO:1)) for this carbohydrate will be tested. Jouault et al. (2001) have described that vaccination with this peptide gave anti-*Candida* antibodies.

EXAMPLE 13

Distribution of DC-SIGN and LFA-1 on the Cell Membrane

Dendritic cells are not only equipped with a highly specialized antigen presentation machinery, but they also possess a unique mechanism that enables them to migrate into tissues and to reach lymphoid compartments when activated to present antigen. Due to the low number of DC present in the peripheral blood, DC were generated from human monocytes after culture in the presence of GM-CSF and IL-4. In addition to the known alterations in chemokine receptors, in performing experiments it was noticed that there were major phenotypical switches in adhesion molecules upon dendritic cell development and maturation. Interestingly, it was observed that LFA-1 as well as the other β$_2$-integrins p150.95 and MAC-1 lose their ability to bind to ICAM-1, although the expression levels of these receptors are increased. Moreover, LFA-1 becomes unable to bind to ICAM-3; in fact, the binding to this molecule on DC is completely DC-SIGN dependent.

To explain these differences in adhesive properties, the cell surface distribution of these receptors was investigated. Employing high resolution microscopy techniques, including electron microscopy and near-field scanning optical microscopy, clearly distinct patterns of distribution of LFA-1 in comparison with DC-SIGN on these cell types were observed. The distribution in defined microdomains on the cell surface directly correlates with ligand binding.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Aderem A and Underhill D M (1999). *Annu. Rev. Immunol.* 17:593-623.
Alvarez C P, et al. (2002). *J. Virol.* 76:6841-6844.
Baribaud F, et al. (2001). *Virology* 286:1-6.
Bates E E, et al. (1999). *J. Immunol.* 163:1973-1983.
Colmenares M, et al. (2002). *J. Biol. Chem.* (e-publication ahead of print, manuscript M205270200 published Jul. 16, 2002).
Curtis B M, et al. (1992). *Proc. Natl. Acad. Sci. USA* 89:8356-8360.
d'Ostiani C F, et al. (2000). *J. Exp. Med.* 191:1661-1673.
Edwards J E (1991). *N. Engl. J. Med.* 324:1060-1062.
Engering A, et al. (2002). *J. Immunol.* 168:2118-2126.
Figdor C G, et al. (2002). *Nat. Rev. Immunol.* 2:77-84.
Forsyth C B and Mathews H L (1996). *Cell. Immunol.* 170:91-100.
Forsyth C B, et al. (1998). *J Immunol.* 161:6198-6205.
Geijtenbeek T B, et al. (1999). *Blood* 94:754-764.
Geijtenbeek T B, et al. (2000a). *Cell* 100:575-585.
Geijtenbeek T B, et al. (2000b). *Cell* 100:587-597.
Geijtenbeek T B, et al. (2000c). *Nat. Immunol.* 1:353-357.
Huang Q, et al. (2001). *Science* 294:870-875.
Huse W D, et al. (1989). *Science* 246:1275-1281.
Janeway-Travers: "*Immunobiology the immune system in health and disease*", Third Edition.
Jouault T, et al. (2001). *Glycobiology* 11:693-701.
Marth T and Kelsall B L (1997). *J. Exp. Med.* 185:1987-1995.
Medzhitov R and Janeway C (2000). *Trends Microbiol.* 8:452-456.
Mosser D M and Karp C L (1999). *Curr. Opin. Immunol.* 11:406-411.
Nelissen J M, et al. (2000). *Mol. Biol. Cell* 11:2057-2068.
Newman S L and Holly A (2001). *Infect. Immun.* 69:6813-6822.
Odds F C (1987). *Crit. Rev. Microbiol.* 15:1-5.
Roitt I, et al. (1994). "*Immunology*", 2nd Ed., Churchill Livingstone.
Sallusto F, et al. (1995). *J. Exp. Med.* 182:389-400.
Shibata N, et al. (1985). *Arch. Biochem. Biophys.* 243:338-348.
Shibata N, et al. (1996). *J. Biol. Chem.* 271:9259-9266.
Shibata Y, et al. (1997). *J. Immunol.* 159:2462-2467.
Sites D P, et al. (1994). "*Basic and clinical immunology*", 8th Ed., Prentice-Hall.
Steinman R M (1991). *Annu. Rev. Immunol.* 9:271-296.
Steinman R M (2000). *Cell* 100:491-494.
Sternberg S (1994). *Science* 266:1632-1634.
Szabo I, et al. (1995). *Cell. Immunol.* 164:182-188.
Vazeux R, et al. (1992). *Nature* 360:485-488.
Vidarsson G and van de Winkel J G J (1998). *Curr. Opin. Infect. Dis.* 11:271-283.
Vissers J L, et al. (2001). *J. Leukoc. Biol.* 69:785-793.
Yamamoto Y, et al. (1997). *Infect. Immun.* 65:1077-1082.
U.S. Pat. No. 6,548,275
WO 93/01820
WO 95/32734
WO 96/23882
WO 98/02456
WO 98/41633
WO 98/49306
WO 00/63251
WO 02/50119

The invention claimed is:

1. A method for treating a subject suffering from an infection with a yeast or fungus that binds to DC-specific ICAM-grabbing non-integrin (DC-SIGN), said method comprising administering to a subject in need thereof an antibody that binds DC-SIGN in an amount effective to inhibit the binding of said yeast or fungus to DC-SIGN.

2. The method of claim 1 wherein said antibody inhibits binding of β-1,2-oligomannoside to DC-SIGN.

3. The method of claim 1 wherein said yeast is *Candida*.

4. The method of claim 3 wherein said yeast is the species *Candida albicans, Candida dubliniensis* or *Candida glabrata*.

5. The method of claim 1 wherein said fungus is *Aspergillus fumigatus*.

6. The method of claim 1 wherein said subject is a human.

7. The method of claim 1 wherein said antibody is the antibody produced by the hybridoma cell line deposited as ECACC accession number 99040818, the antibody produced by the hybridoma cell Line deposited as ECACC accession number 99040819, or the antibody produced by the hybridoma cell line deposited as ECACC accession number 03071801.

8. The method of claim 1 wherein two or more antibodies that inhibit binding of the yeast or fungus to DC-SIGN are administered in combination.

9. A method of inhibiting infection by a yeast or fungus in a subject comprising administering to a subject in need thereof an antibody that binds DC-SIGN wherein said antibody at least partially inhibits binding of an infection-causing yeast or fungus to DC-SIGN on dendritic cells.

10. The method of claim 9 wherein more than one antibody that inhibits binding is administered.

11. The method of claim 9 wherein said antibody inhibits binding of β-1,2-ligomannoside to DC-SIGN.

12. The method of claim 9 wherein said yeast is *Candida*.

13. The method of claim 12 wherein said yeast is the species *Candida albicans, Candida dubliniensis or Candida glabrata*.

14. The method of claim 9 wherein said fungus is *Aspergillus fumigatus*.

15. The method of claim 9 wherein said subject is a human.

16. The method of claim 9 wherein said antibody is the antibody produced by the hybridoma cell line deposited as ECACC accession number 99040818, the antibody produced by the hybridoma cell line deposited as ECACC accession number 99040819, or the antibody produced by the hybridoma cell line deposited as ECACC accession number 03071801.

* * * * *

UNITED STATES PATENT AND TRADEMARK OFFICE
CERTIFICATE OF CORRECTION

PATENT NO. : 7,541,032 B2
APPLICATION NO. : 10/524395
DATED : June 2, 2009
INVENTOR(S) : Figdor et al.

Page 1 of 1

It is certified that error appears in the above-identified patent and that said Letters Patent is hereby corrected as shown below:

Claim 7, Col. 17, line 38, delete "cell Line deposited" and instead insert --cell line deposited--;

Claim 11, Col. 18, line 28, delete "β-1,2-ligomannoside" and instead insert --β-1,2-oligomannoside--.

Signed and Sealed this

Eleventh Day of August, 2009

David J. Kappos
*Director of the United States Patent and Trademark Office*